(12) United States Patent
Tipirneni

(10) Patent No.: US 8,702,768 B2
(45) Date of Patent: Apr. 22, 2014

(54) CANNULATED BONE SCREW SYSTEM AND METHOD

(75) Inventor: Kishore Tipirneni, Glendale, AZ (US)

(73) Assignee: Orthoip, LLC, Boca Raton, FL (US)

( * ) Notice: Subject to any disclaimer, the term of this patent is extended or adjusted under 35 U.S.C. 154(b) by 897 days.

(21) Appl. No.: 11/742,457

(22) Filed: Apr. 30, 2007

(65) Prior Publication Data

US 2007/0260248 A1    Nov. 8, 2007

Related U.S. Application Data

(63) Continuation-in-part of application No. 11/678,473, filed on Feb. 23, 2007, which is a continuation-in-part of application No. 10/779,892, filed on Feb. 17, 2004, which is a continuation of application No. 10/272,773, filed on Oct. 17, 2002, now Pat. No. 6,736,819.

(60) Provisional application No. 60/330,187, filed on Oct. 18, 2001.

(51) Int. Cl.
     *A61B 17/86*      (2006.01)

(52) U.S. Cl.
     USPC .......................................................... 606/320

(58) Field of Classification Search
     USPC ................... 606/300, 310, 320, 327, 328, 65;
                              411/383, 384, 392
     See application file for complete search history.

(56) References Cited

U.S. PATENT DOCUMENTS

| | | | |
|---|---|---|---|
| 1,025,008 A | 4/1912 | Miner | |
| 2,077,804 A | 4/1937 | Morrison | |
| 2,381,050 A | 8/1945 | Hardinge | |
| 2,397,545 A | 4/1946 | Hardinge | |
| 2,414,882 A | 1/1947 | Longfellow | |
| 2,490,364 A | 12/1949 | Livingston | |
| 2,511,051 A | 6/1950 | Dzus | |
| 3,051,169 A * | 8/1962 | Grath | 606/65 |
| 3,433,220 A | 3/1969 | Zickel | |
| 3,489,143 A | 1/1970 | Halloran | |
| 4,456,005 A * | 6/1984 | Lichty | 606/60 |

(Continued)

FOREIGN PATENT DOCUMENTS

| | | |
|---|---|---|
| FR | 2784019 | 4/2000 |
| WO | WO 00/67652 | 11/2000 |
| WO | WO2007125561 | 11/2008 |
| WO | WO200915075 | 12/2009 |

OTHER PUBLICATIONS

Notice of Allowance mailed Feb. 20, 2004 in U.S. Appl. No. 10/272,773.

(Continued)

*Primary Examiner* — Christian Sevilla
(74) *Attorney, Agent, or Firm* — Snell & Wilmer L.L.P.

(57) ABSTRACT

An improved bone screw is disclosed which includes a shaft with distal portion having a threaded surface thereon, a sleeve having an opening which receives the shaft such that the shaft is able to move within the sleeve without moving the sleeve. A compressive device may be incorporated between the sleeve and the proximal portion of the shaft such that the compressive device forces the shaft and sleeve towards each other, thereby maintaining the compressive load at the union of the fracture. As additional compression is exerted on the load from weight bearing, the force may be reduced, but the head of the sleeve is still substantially maintained against the lateral cortex.

16 Claims, 16 Drawing Sheets

(56) References Cited

U.S. PATENT DOCUMENTS

| | | | |
|---|---|---|---|
| 4,617,922 A | 10/1986 | Griggs | |
| 4,621,629 A * | 11/1986 | Koeneman | 606/65 |
| 4,632,100 A | 12/1986 | Somers et al. | |
| 4,640,271 A | 2/1987 | Lower | |
| 4,708,132 A | 11/1987 | Silvestrini | |
| 4,741,330 A | 5/1988 | Hayhurst | |
| 4,773,406 A | 9/1988 | Spector et al. | |
| 4,858,601 A * | 8/1989 | Glisson | 606/916 |
| 4,863,383 A * | 9/1989 | Grafelmann | 433/174 |
| 4,889,110 A | 12/1989 | Galline | |
| 4,905,680 A | 3/1990 | Tunc | |
| 4,934,935 A * | 6/1990 | Edwards | 433/174 |
| 4,940,467 A * | 7/1990 | Tronzo | 606/66 |
| 4,959,064 A * | 9/1990 | Engelhardt | 606/65 |
| 5,019,079 A | 5/1991 | Ross | |
| 5,041,116 A | 8/1991 | Wilson | |
| 5,061,137 A | 10/1991 | Gourd | |
| 5,100,405 A | 3/1992 | McLaren | |
| 5,102,276 A * | 4/1992 | Gourd | 411/392 |
| 5,116,336 A * | 5/1992 | Frigg | 606/68 |
| 5,116,340 A | 5/1992 | Songer | |
| 5,122,133 A | 6/1992 | Evans | |
| 5,127,914 A | 7/1992 | Calderale et al. | |
| 5,129,901 A | 7/1992 | Decoste | |
| 5,141,520 A | 8/1992 | Goble et al. | |
| 5,207,753 A | 5/1993 | Badrinath | |
| 5,217,462 A | 6/1993 | Asnis et al. | |
| 5,269,784 A | 12/1993 | Mast | |
| 5,300,075 A | 4/1994 | Gordon | |
| 5,306,290 A | 4/1994 | Martins et al. | |
| 5,324,292 A | 6/1994 | Meyers | |
| 5,336,028 A | 8/1994 | Yamamoto | |
| 5,338,139 A | 8/1994 | Swanstrom | |
| 5,364,398 A | 11/1994 | Chapman et al. | |
| 5,368,605 A | 11/1994 | Miller | |
| 5,382,124 A | 1/1995 | Frattarola | |
| 5,409,493 A | 4/1995 | Greenberg | |
| 5,417,692 A | 5/1995 | Goble et al. | |
| 5,423,820 A | 6/1995 | Miller et al. | |
| 5,431,660 A | 7/1995 | Burke | |
| 5,462,547 A | 10/1995 | Weigum | |
| 5,507,801 A | 4/1996 | Gisin | |
| 5,520,691 A | 5/1996 | Branch | |
| 5,586,985 A * | 12/1996 | Putnam et al. | 606/86 B |
| 5,591,207 A | 1/1997 | Coleman | |
| 5,601,553 A | 2/1997 | Trebing et al. | |
| 5,607,426 A | 3/1997 | Ralph et al. | |
| 5,611,801 A | 3/1997 | Songer | |
| 5,632,745 A | 5/1997 | Schwartz | |
| 5,643,267 A | 7/1997 | Hitomi et al. | |
| 5,702,397 A | 12/1997 | Goble et al. | |
| 5,709,687 A | 1/1998 | Penning | |
| 5,725,582 A | 3/1998 | Bevan | |
| 5,809,849 A | 9/1998 | Coffey et al. | |
| 5,810,821 A * | 9/1998 | Vandewalle | 606/65 |
| 5,827,285 A | 10/1998 | Bramlet | |
| 5,893,850 A | 4/1999 | Cachia | |
| 5,893,859 A | 4/1999 | Marin et al. | |
| 5,899,906 A * | 5/1999 | Schenk | 606/301 |
| 5,902,011 A * | 5/1999 | Hand et al. | 297/284.6 |
| 5,928,236 A | 7/1999 | Augagneur et al. | |
| 5,954,722 A | 9/1999 | Bono | |
| 5,964,760 A | 10/1999 | Richelsoph | |
| 5,964,763 A | 10/1999 | Incavo et al. | |
| 5,976,139 A | 11/1999 | Bramlet | |
| 5,984,925 A | 11/1999 | Apgar | |
| 5,993,477 A | 11/1999 | Vaitekunas et al. | |
| 5,997,538 A | 12/1999 | Asnis et al. | |
| 5,997,541 A | 12/1999 | Schenk | |
| 6,027,523 A | 2/2000 | Schmieding | |
| 6,033,429 A | 3/2000 | Magovern | |
| 6,039,740 A | 3/2000 | Olerud | |
| 6,050,998 A | 4/2000 | Fletcher | |
| 6,093,188 A | 7/2000 | Murray | |
| 6,143,037 A | 11/2000 | Goldstein et al. | |
| 6,171,310 B1 | 1/2001 | Giordano | |
| 6,174,006 B1 | 1/2001 | Burt | |
| 6,183,474 B1 | 2/2001 | Bramlet | |
| 6,235,062 B1 | 5/2001 | Grammas | |
| 6,245,071 B1 | 6/2001 | Pierson | |
| 6,251,111 B1 | 6/2001 | Barker et al. | |
| 6,319,254 B1 | 11/2001 | Giet et al. | |
| 6,348,053 B1 | 2/2002 | Cachia | |
| 6,368,326 B1 | 4/2002 | Dakin et al. | |
| 6,524,313 B1 | 2/2003 | Fassier et al. | |
| 6,602,293 B1 | 8/2003 | Biermann et al. | |
| 6,605,090 B1 | 8/2003 | Trieu et al. | |
| 6,610,067 B2 | 8/2003 | Schenk | |
| 6,629,534 B1 | 10/2003 | St. Goar et al. | |
| 6,632,224 B2 | 10/2003 | Cachia et al. | |
| 6,656,184 B1 * | 12/2003 | White et al. | 606/318 |
| 6,656,185 B2 | 12/2003 | Gleason et al. | |
| 6,685,706 B2 | 2/2004 | Padget et al. | |
| 6,695,844 B2 | 2/2004 | Bramlet | |
| 6,736,819 B2 | 5/2004 | Tipirneni | |
| 6,840,953 B2 | 1/2005 | Martinek | |
| 6,887,243 B2 | 5/2005 | Culbert | |
| 6,887,271 B2 | 5/2005 | Justin et al. | |
| 6,890,333 B2 | 5/2005 | von Hoffmann et al. | |
| 6,902,567 B2 | 6/2005 | Del Medico | |
| 6,908,465 B2 | 6/2005 | von Hoffmann et al. | |
| 6,984,241 B2 | 1/2006 | Lubbers et al. | |
| 7,008,428 B2 | 3/2006 | Cachia et al. | |
| 7,033,363 B2 | 4/2006 | Powell | |
| 7,070,601 B2 | 7/2006 | Culbert et al. | |
| 7,090,686 B2 | 8/2006 | Huebner et al. | |
| 7,094,239 B1 | 8/2006 | Michelson | |
| 7,094,240 B2 | 8/2006 | Molz et al. | |
| 7,135,023 B2 | 11/2006 | Watkins | |
| 7,147,639 B2 | 12/2006 | Berki et al. | |
| 7,163,542 B2 | 1/2007 | Ryan | |
| 7,172,595 B1 | 2/2007 | Goble | |
| 7,189,251 B2 | 3/2007 | Kay | |
| 7,476,254 B2 | 1/2009 | White et al. | |
| 7,591,823 B2 | 9/2009 | Tipirneni | |
| 7,641,677 B2 | 1/2010 | Weiner et al. | |
| 7,771,428 B2 | 8/2010 | Siravo et al. | |
| 2002/0198527 A1 | 12/2002 | Muckter | |
| 2003/0036761 A1 | 2/2003 | Smothers et al. | |
| 2003/0083658 A1 | 5/2003 | Hawkes et al. | |
| 2003/0187440 A1 | 10/2003 | Richelsoph et al. | |
| 2003/0216780 A1 | 11/2003 | Fitts et al. | |
| 2004/0097943 A1 | 5/2004 | Hart | |
| 2004/0127906 A1 | 7/2004 | Culbert et al. | |
| 2004/0236424 A1 | 11/2004 | Berez et al. | |
| 2004/0243129 A1 | 12/2004 | Moumene et al. | |
| 2005/0010226 A1 | 1/2005 | Grady, Jr. et al. | |
| 2005/0234456 A1 | 10/2005 | Malandain | |
| 2005/0263549 A1 | 12/2005 | Scheiner | |
| 2006/0129148 A1 | 6/2006 | Simmons et al. | |
| 2006/0147127 A1 | 7/2006 | Slavin | |
| 2006/0161805 A1 | 7/2006 | Tseng | |
| 2006/0167457 A1 | 7/2006 | Suddaby | |
| 2006/0190001 A1 | 8/2006 | Powell | |
| 2006/0248638 A1 | 11/2006 | Trieu et al. | |
| 2006/0264954 A1 * | 11/2006 | Sweeney et al. | 606/73 |
| 2007/0055249 A1 | 3/2007 | Jensen et al. | |
| 2007/0123878 A1 | 5/2007 | Shaver | |
| 2007/0162019 A1 | 7/2007 | Burns et al. | |
| 2007/0162026 A1 | 7/2007 | Tipirneni et al. | |
| 2007/0190230 A1 | 8/2007 | Trieu | |
| 2007/0233100 A1 | 10/2007 | Metzinger | |
| 2007/0260248 A1 | 11/2007 | Tipirneni | |
| 2007/0270847 A1 | 11/2007 | Shaw | |
| 2007/0276382 A1 | 11/2007 | Mikhail et al. | |
| 2008/0086144 A1 | 4/2008 | Zander | |
| 2008/0147126 A1 | 6/2008 | Tipirneni | |
| 2008/0147127 A1 | 6/2008 | Tipirneni et al. | |
| 2008/0243191 A1 | 10/2008 | Tipirneni et al. | |
| 2008/0255555 A1 | 10/2008 | Justis et al. | |
| 2008/0255621 A1 | 10/2008 | Fricker et al. | |
| 2008/0300636 A1 | 12/2008 | Carli et al. | |
| 2009/0131936 A1 | 5/2009 | Tipirneni et al. | |
| 2009/0131990 A1 | 5/2009 | Tipirneni et al. | |

(56) References Cited

U.S. PATENT DOCUMENTS

| | | | |
|---|---|---|---|
| 2009/0131991 A1 | 5/2009 | Tipirneni et al. |
| 2009/0177199 A1 | 7/2009 | Tipirneni |
| 2009/0198288 A1 | 8/2009 | Hoof et al. |
| 2009/0254089 A1 | 10/2009 | Tipirneni |
| 2009/0254129 A1 | 10/2009 | Tipirneni |
| 2009/0306718 A1 | 12/2009 | Tipirneni |
| 2010/0114097 A1 | 5/2010 | Siravo et al. |
| 2010/0312245 A1 | 12/2010 | Tipirneni et al. |
| 2010/0312292 A1 | 12/2010 | Tipirneni et al. |
| 2011/0034925 A1 | 2/2011 | Tipirneni et al. |
| 2011/0295252 A1 | 12/2011 | Tipirneni et al. |

OTHER PUBLICATIONS

Non-Final Office Action mailed Nov. 16, 2005 in U.S. Appl. No. 10/779,892.
Requirement for Restriction mailed Jul. 18, 2006 in U.S. Appl. No. 10/779,892.
Final Office Action mailed Jan. 3, 2007 in U.S. Appl. No. 10/779,892.
Advisory Action mailed Feb. 2, 2007 in U.S. Appl. No. 10/779,892.
Non-Final Office Action mailed Mar. 1, 2007 in U.S. Appl. No. 10/779,892.
Final Office Action mailed Oct. 31, 2007 in U.S. Appl. No. 10/779,892.
Advisory Action mailed Jan. 22, 2008 in U.S. Appl. No. 10/779,892.
Non-Final Office Action mailed Mar. 4, 2008 in U.S. Appl. No. 10/779,892.
Requirement for Restriction mailed Dec. 10, 2008 in U.S. Appl. No. 10/779,892.
ISR and Written Opinion mailed Jan. 22, 2009 in PCT/US08/84623.
Final Office Action mailed May 14, 2009 in U.S. Appl. No. 10/779,892.
Notice of Allowance mailed Aug. 7, 2009 in U.S. Appl. No. 10/779,892.
Non-Final Office Action mailed Jun. 10, 2009 in U.S. Appl. No. 11/952,413.
Non-Final Office Action mailed Jun. 19, 2009 in U.S. Appl. No. 11/952,715.
Non-Final Office Action mailed Aug. 20, 2009 in U.S. Appl. No. 11/678,473.
Office Action dated Apr. 27, 2011 in U.S. Appl. No. 12/400,165.
Office Action dated May 11, 2011 in U.S. Appl. No. 12/369,589.
International Preliminary Report on Patentability dated Jul. 20, 2011 in Application No. PCT/US2010/023537.
Office Action dated Jun. 22, 2011 in U.S. Appl. No. 12/235,405.
Office Action Restriction dated Jun. 22, 2011 in U.S. Appl. No. 12/163,122.
Final Office Action dated Aug. 16, 2011 in U.S. Appl. No. 12/104,328.
Office Action dated Aug. 17, 2011 in U.S. Appl. No. 12/163,122.
Office Action dated Aug. 19, 2011 in U.S. Appl. No. 12/265,890.
Final Office Action mailed Feb. 19, 2010 in U.S. Appl. No. 11/678,473.
Advisory Acton mailed Apr. 14, 2010 in U.S. Appl. No. 11/678,473.
Final Office Action mailed Jan. 25, 2010 in U.S. Appl. No. 11/952,715.
Advisory Action mailed on Apr. 12, 2010 in U.S. Appl. No. 11/952,715.
Notice to File Missing Parts on May 12, 2010 in U.S. Appl. No. 12/769,529.
Non-Final Office Action issued Dec. 30, 2009 in U.S. Appl. No. 11/952,413.
PCT/US2009/061782 International Search Report and Written Opinion issued Dec. 15, 2009.
PCT/US09/578791 International Search Report and Written Opinion issued Nov. 16, 2009.
URL: http://www.cayennemedical.com/products/ifix/, Title: iFix, Source: Cayenne Medical in U.S. Appl. No. 12/265,890.
PCT-US2010-023537 International Search and Written Opinion Report mailed Apr. 15, 2010.
Non-Final Office Action issued Jun. 28, 2010 in U.S. Appl. No. 12/400,184.
Final Office Action issued Jun. 29, 2010 in U.S. Appl. No. 11/952,413.
Advisory Action issued Sep. 1, 2010 in U.S. Appl. No. 11/952,413.
PCT International Search Report and Written Opinion dated Jan. 22, 2009 .
International Search Report and Written Opinion dated Jul. 7, 2011 in Application No. PCT/US2011/033370.
Notice of Allowance dated Sep. 29, 2011 in U.S. Appl. No. 12/400,165.
Final Office Action dated Oct. 28, 2011 in U.S. Appl. No. 12/369,589.
Office Action dated Nov. 1, 2011 in U.S. Appl. No. 12/425,225.
Office Action dated Nov. 10, 2011 in U.S. Appl. No. 12/491,132.
Office Action dated Nov. 10, 2011 in U.S. Appl. No. 12/258,013.
Office Action dated Sep. 2, 2011 in U.S. Appl. No. 12/104,658.
Final Office Action dated Dec. 7, 2011 in U.S. Appl. No. 12/235,405.
Final Office Action dated Feb. 1, 2012 in U.S. Appl. No. 12/265,890.
USPTO; Notice of Allowance dated Dec. 14, 2010 in U.S. Appl. No. 12/400,184.
PCT; International Preliminary Report on Patentability dated Jul. 15, 2010 in Application No. PCT/US2008/084623.
International Preliminary Report on Patentability dated Jan. 31, 2011 in Application No. PCT/US2009/061782.
International Preliminary Report on Patentability dated Jan. 31, 2011 in Application No. PCT/US2009/057879.
Office Action dated Mar. 17, 2011 in U.S. Appl. No. 12/104,658.
Office Action dated Mar. 8, 2011 in U.S. Appl. No. 12/104,328.

* cited by examiner

CANNULATED BONE SCREW SYSTEM AND METHOD

CROSS-REFERENCE TO RELATED APPLICATIONS

This application is a continuation-in-part of U.S. Ser. No. 11/678,473, which itself is a continuation-in-part of, and claims priority to, U.S. Ser. No. 10/779,892 filed on Feb. 17, 2004 and entitled System And Method For The Fixation Of Bone Fractures which itself claims priority to U.S. Ser. No. 10/272,773 filed on Oct. 17, 2002 with the same title (now U.S. Pat. No. 6,736,819). The '819 patent itself claims priority to U.S. Provisional Application Ser. No. 60/330,187, entitled Lagwire System And Method filed Oct. 18, 2001, all of which are incorporated herein by reference.

FIELD OF INVENTION

The invention generally relates to a system and method for the fixation of fractures in one or more objects, and more particularly, to a bone screw for the fixation of bone fractures which collapses along with the fracture collapse to minimize protrusion of the device beyond the bone surface, and to maintain compression across the fracture during fracture collapse.

BACKGROUND OF THE INVENTION

It is well-known in the medical arts that constant pressure on a bone fracture speeds healing. As such, orthopedic physicians typically insert one or more screws in the area of the fracture in order to assert constant pressure on the bone fracture. However, the insertion of existing screws through or around fractures has disadvantages. For example, the entire process is very time-consuming because inserting a regular screw usually involves multiple steps such as drilling the pilot hole, measuring the relevant distances to determine the appropriate screw selection, tapping the hole to establish threads and screwing the screw into the hole. Moreover, when using a bone screw, the process usually includes even more steps such as drilling through the near cortex to establish the guiding hole (e.g., 3.5 mm), placing the drill guide in the proper location, drilling through the far cortex (e.g., 2.5 mm), measuring the distance to determine the appropriate screw selection, tapping the hole to establish threads and rotating the screw into the hole, thereby attempting to compress the fracture. Again, each step and the entire process is very time-consuming.

In addition to the length and complexity of the process, the prior art system also typically includes inadequate components. For example, in poor bone, prior art screws often loose their grip and strip out of the bone. Currently available bone screws also typically provide only one side of cortex fixation and are generally not suited for percutaneous surgery. Moreover, when placing the screws in the bone, the physician may not accurately set the screw into the distal hole or may miss the distal hole completely, thereby resulting in the screw stripping the threads or breaking the bone.

Furthermore, the location and extent of most every fracture is unique, so different screws are often needed for each fracture. Because the physician typically is unable to accurately determine the type or size of screw needed until the physician enters the bone and measures the appropriate screw placement, operating facilities need to store and make available large inventories of screws. Particularly, screws usually range in length from about 10 mm to about 75 mm with available screw sizes limited to every 2 mm there between. Moreover, for each size of screw, the screws may be either a cancellous or cortical type, and for each size and type of screw, the screw may include one of three different pitches. Accordingly, a screw set typically exceeds one hundred screws. Furthermore, if cannulated screws are desired, another entire screw set of over one hundred additional screws is often needed. Moreover, each time a screw from a screw set is utilized in a procedure, a replacement screw is typically obtained to complete the set. As such, inventory management of screws is a very large problem for many operating facilities. A need exists for a lagwire system which simplifies and expedites the process for the fixation of bone fractures, while minimizing the number of components needed in the process.

Additionally, in hip fractures (e.g. femoral neck fracture), the non-union rate is about 25-30%. Certain factors may contribute to the non-union rate in fractures such as, for example, poor blood supply and age of patient. However, an important factor for the non-union rate in fractures is micro-motion. Micro-motion of the hip bones is typically caused by the natural movements of the patient while the patient is walking, hopping on crutches, twisting and the like. Such micro-motion has an affect on the bone screw in that the micro-motion often causes the bone screw to slide within the bone, thereby disrupting the bone union. The bone union is disrupted because the union loses its fixed compression and fracture interface is decompressed.

Another concern with bone screws is that the head of bone screw often protrudes out of the bone surface over time. In particular, when a bone fracture is set with a bone screw, the bone screw typically does not completely compress the bone fragments together. As such, after the patient stands and a weight bearing force is applied against the bone fragments (or any other compressive forces applied to the bone fragments), the fragments are further compressed. The further compression of the bone fragments results in the head of the bone screw (which was previously flush with the outside surface of the bone) protruding outside from the surface of the bone. In some cases, the head of the bone screw may protrude about 1 cm which may result in pain and/or the need for additional surgery. A need exists for a device and method for maintaining the initial and subsequent compression of a bone fracture to increase the union rate of the bone fracture.

SUMMARY OF THE INVENTION

In general, the invention facilitates the fixation of bone fractures. In one embodiment, the head component includes a tip, cutting threads and mating threads which are inserted into the far cortex of the bone. A wire extends from the head component and exits from the near cortex.

A cap device fits over the other end of the wire such that the cap device permits travel of the cap in one direction (e.g., distal travel with respect to the wire), but resists travel of the cap in the other direction (e.g., proximal travel with respect to the wire). In one embodiment, a cap device having a sawtooth inner surface is threaded over the wire having an inverse sawtooth outer surface such that the cap is restricted from backwards movement. In another embodiment, the cap includes a circular tension spring inside the cap such that the wire is received within a central opening within the circular tension spring. The tension spring also includes a nub extending from the outer circumference of the tension spring such that a portion of the inner circumference of the tension spring provides friction against the wire only one way (when the cap is pulled proximal, away from the bone). The friction is asserted against the wire because the nub on the side of the tension spring hits the top circular cap, so it forces the tension spring to flex and assert friction on the wire. When the cap is pushed the other way (e.g., when the cap is pushed distal, toward the bone) the nub of the tension spring is forced down, so it does not engage any surface, and the wire is able to translate, with minimal or no friction, through the central opening in the tension spring.

Tension is then applied to the wire while the cap is tightened against or within the bone surface to thereby apply an appropriate amount of pressure between the surfaces of the fracture. The excess wire beyond the cap can then be removed.

The invention also includes a system for facilitating a change in distance between objects, wherein the system includes a head component configured to attach to one of the objects; a wire having a first end and a second end, wherein the first end of the wire is configured to mate with the head component; and, a cap configured to mate with the second end of the wire. The invention also includes a method for facilitating a change in distance between a first and second surface The method includes providing a head component mated with a wire having a first interface component; inserting the head component into the first surface by mating a drill over a driver head of the head component to facilitate drilling the head component into the bone and cutting new threads into the object using the cutting threads and mating the new threads with the mating threads; extending the wire through the second surface; threading a cap having a second interface component over the first interface component of the wire; and removing the excess wire beyond the cap.

In another embodiment, the invention includes a shaft with distal portion having a threaded surface thereon, a sleeve having an opening which receives the shaft such that the shaft is able to move within the sleeve with minimal or no movement of the sleeve. In one embodiment, a compressive device (e.g., spring) exists between the sleeve and the proximal portion of the shaft such that the compressive device exerts a force directly or indirectly against the shaft and the sleeve. In one embodiment, the compressive device is located inside the sleeve. The compressive device exerts a force which serves to move the distal head and the proximal sleeve toward each other, thereby maintaining the compressive load at the union of the fracture. As additional compression is exerted on the fracture from weight bearing, the force may be reduced, but the head of the sleeve is still substantially maintained against the lateral cortex. The sleeve may be maintained against the lateral cortex until sufficient collapse of the fracture occurs such that the compressive device no longer exerts a force against the sleeve or shaft, then the device may simply act as a traditional bone screw. As such, the improved bone screw of the present invention minimizes or prevents the device from protruding beyond the bone, and maintains the compression across the fracture during fracture collapse. The bone screw of the present invention may be used in place of any existing bone screw, or any existing component of a product that performs a similar function as a bone screw.

BRIEF DESCRIPTION OF THE DRAWINGS

A more complete understanding of the present invention may be derived by referring to the detailed description and claims when considered in connection with the figures, wherein like reference numbers refer to similar elements throughout the figures, and:

DETAILED DESCRIPTION

The present invention is described herein and includes various exemplary embodiments in sufficient detail to enable those skilled in the art to practice the invention, and it should be understood that other embodiments may be realized without departing from the spirit and scope of the invention. Thus, the following detailed description is presented for purposes of illustration only, and not of limitation, and the scope of the invention is defined solely by the appended claims. The particular implementations shown and described herein are illustrative of the invention and its best mode and are not intended to otherwise limit the scope of the present invention in any way.

In general, the present invention facilitates the change in distance between objects or surfaces, compresses objects together and/or provides a configurable or random amount of pressure between surfaces. The system may facilitate changing, maintaining, reducing and/or expanding the distance between objects. The applied pressure may be suitably configured to be constant, increasing, decreasing, variable, random, and/or the like. In an exemplary embodiment, the invention includes a device which may be fixedly or removably attached to pathology, such as to a certain portion of a bone. In a particular embodiment, the device is fixedly or removably attached to the far cortex of the bone. In another embodiment, the invention includes a device or method for retracting the attached device to reduce the distance between the surfaces of the pathology. In a further embodiment, the invention includes a device and/or method for maintaining the pressure between the surfaces of pathology.

Figure 1:
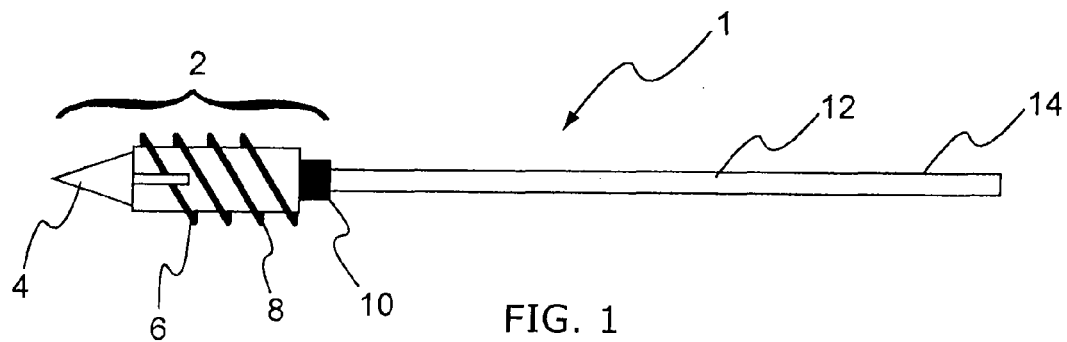
FIG. 1 is a lagwire system including a head component and wire in accordance with an exemplary embodiment of the present invention.

In an exemplary embodiment, and as shown in FIGS. 1 and 2, the lagwire system 1 includes a head component 2, a wire 12 and a cap 20. The lagwire system 1 may be fabricated using any type, amount or combination of materials suitably configured for the particular application. In an exemplary embodiment for medical applications, the lagwire system 1 is fabricated with stainless steel, titanium and/or titanium alloy which minimize reactivity with the body. Each component may be fabricated with various diameters, thread pitches, lengths and/or the like.

Certain exemplary components of the system will now be discussed. The head component 2 is any device which is configured to fixedly or removably attach to any object, such as pathology. In a particular embodiment, the head component 2 is configured to be fixedly or removably attached to the far cortex of the bone, as shown in FIGS. 4A-4G. As best shown in FIG. 1, the head component 2 may include, for example, a self drilling tip 4 device which is suitably configured to puncture a hole and/or guide the head component 2, self cutting threads 6 which are suitably configured to cut thread grooves into the inside surface of a hole, fastening threads 8 which are suitably configured to mate with the newly formed thread grooves, and a tool attachment 10 suitably configured for mating with a tool head (e.g., hex head wrench, socket wrench, Phillips screwdriver, flathead screwdriver, allan wrench and/or the like). Head component 2 may include different thread configurations, lengths, diameters, pitches and the like to facilitate insertion into different types of bone or other structures (e.g., cortical bone, cancellous bone, etc).

In a particular embodiment, the tip is on the front end of head component 2, followed by the cutting threads 6, the fastening threads 8, the tool attachment 10, then wire 12. The elements of head component 2 may be fabricated as one component or one or more elements may be configured to be removably or fixedly mated together to form head component 2. If mated together, a particular element may be exchanged for different applications. For example, if head component 2 needs to be inserted into a dense or hard bone, a stronger or sharper tip 4 may be screwed into thread element 6,8. Moreover, if deeper thread grooves are desired, cutting threads 6 may be replaced with greater diameter threads. Furthermore, if a different tool head is incorporated into a drill, tool attachment 10 may be exchanged with the appropriate attachment.

In one embodiment, the outside diameter of the fastening threads are similar to the thread diameters of known surgical screw sizes. Exemplary outside diameters of cortical head components include 3.5 mm and 4.5 mm, wherein the length of the thread section is similar to the cortex thickness. Exemplary outside diameters of cancellous (i.e., little or no cortex) head components include about 4.0 mm and 6.5 mm, wherein the length of the thread section may be about 16 mm or 32 mm.

Wire 12 is any device suitably configured, when force is applied, to reduce the distance between two surfaces. In one embodiment, wire 12 is configured to retract the head component 2 device to reduce the distance between the surfaces of the pathology. In one embodiment, head component 2 and wire 12 are constructed as one component. In another embodiment, head component 2 and wire 12 are constructed as separate components, but the components are configured such that the head component 2 may be threaded onto wire 12 after wire 12 is placed into the bone. Wire 12 further includes an interface component 14 on at least a portion of its surface, wherein the interface component 14 is suitably configured to limit the movement of cap 20 to move distally toward head component 2, but not proximally (backwards).

In an exemplary embodiment, interface component 14 of wire 12 includes a sawtooth like configuration such that one side of each tooth (e.g. the side closest to head component 2) is substantially perpendicular to the surface of wire 12, while the other side of the sawtooth is at a suitable angle, such as 45 degrees, thereby forming a triangular pattern for each sawtooth. In this manner, the inverse sawtooth on the inside surface of the cap slides or bends over the angled side of the wire sawtooth, but the substantially perpendicular side of the wire sawtooth restricts or limits the cap sawtooth from backwards movement. In another embodiment, any portion or the entire length of wire 12 includes any configuration such as, for example, round, oval, flat on one or more portions of the wire, and/or microgrooves or ridges along the wire (which may include the sawtooth configuration, indentions or other configurations) to increase the friction along the wire. In one embodiment, wire 12 holds 20 pounds of pull; however, microgrooves in the wire may significantly increase the strength of the wire 12.

In an exemplary embodiment, wire 12 is comprised of a thin metal such as, for example, stainless steel, titanium and/or titanium alloy, so it may be easily cut to almost any desired length, thereby eliminating or reducing the need for fixed lengths screws. As such, the invention substantially reduces or eliminates the need for the inventory or availability of large screw sets or multiple screws. Moreover, because the system may include numerous materials, configurations and designs for either wire 12 or cap 20, the invention provides increased versatility because the physician is provided with multiple options and choices for wire 12 and cap 20 combinations.

Figure 2A:
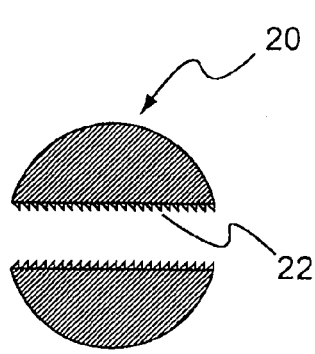
FIG. 2A is a quick cap in accordance with an exemplary embodiment of the present invention.
Figure 2B:
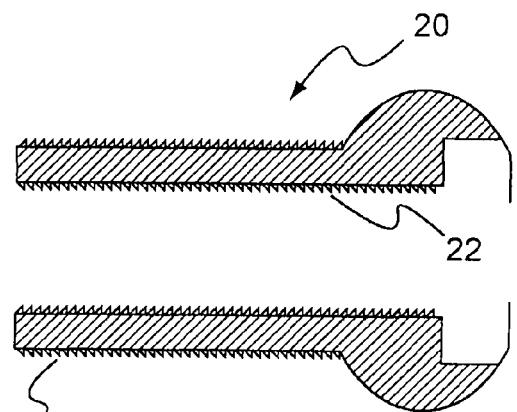
FIG. 2B is an alternative embodiment of a quick cap in accordance with an exemplary embodiment of the present invention.
Figure 2C:
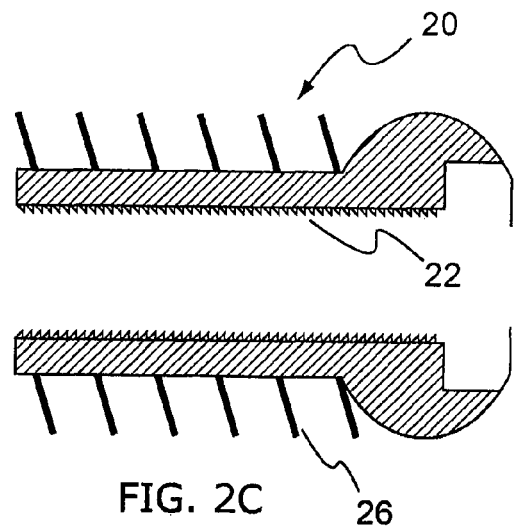
FIG. 2C is a screw cap in accordance with an exemplary embodiment of the present invention.
Figure 2D:
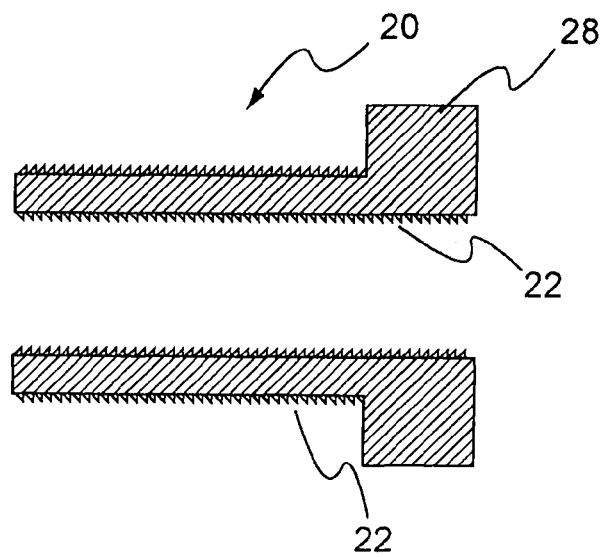
FIG. 2D is a flat cap in accordance with an exemplary embodiment of the present invention.

Cap 20 is any device suitably configured to maintain or increase the pressure between the surfaces of pathology by limiting wire 12 movement. As shown in FIGS. 2A-2E, exemplary caps 20 may include various configurations, materials, shapes and/or sizes. In one embodiment, and as shown in FIG. 2A, cap 20 includes an inverse interface component 22 relative to wire 12 interface component such that cap 20 is restricted from backwards translation after cap 20 is inserted over wire 12. In one embodiment, the interface component 22 on cap 20 is located at least on the inside surface of the cap and includes a saw tooth pattern with the same or similar pitch as the saw tooth on wire 12. This configuration also allows cap 20 to slide along wire 12 without the need for spinning cap 20 which is important because time is of the essence in a medical procedure and spinning the cap down a sufficiently long length of wire would be very time-consuming. Examples of cap 20 include a screw cap 20, flat cap 20 and a quick cap 20. As shown in FIG. 2C, screw cap 20 is configured with teeth 22, cutting threads 24 and/or mating threads 26 on the outside surface to facilitate rotating cap 20 into the cortex to, for example, fix surgical plates against certain pathology. However, cutting threads 24 may not be needed on any of the caps because cutting threads 6 of head component 2 may have already tapped the threads on the inside surface of the bone, so the teeth 22 or mating threads 26 alone can simply rotatably engage the threads formed from cutting threads 6 and provide sufficient friction to secure the cap in the bone. As shown in FIG. 2D, flat cap 20 may include teeth 22, cutting threads 24 and/or mating threads 26 on the outside surface to facilitate rotating cap 20 into the cortex, but it also is configured with a flat top surface 28 to allow cap 20 to be inserted into the cortex such that the flat top surface 28 of cap 20 does not substantially protrude from the cortex surface. As best shown in FIG. 2A, for example, the quick cap 20 or any other cap may be configured with only the interface component on the inside surface, thereby allowing for quick and easy assembly.

Figure 2E:
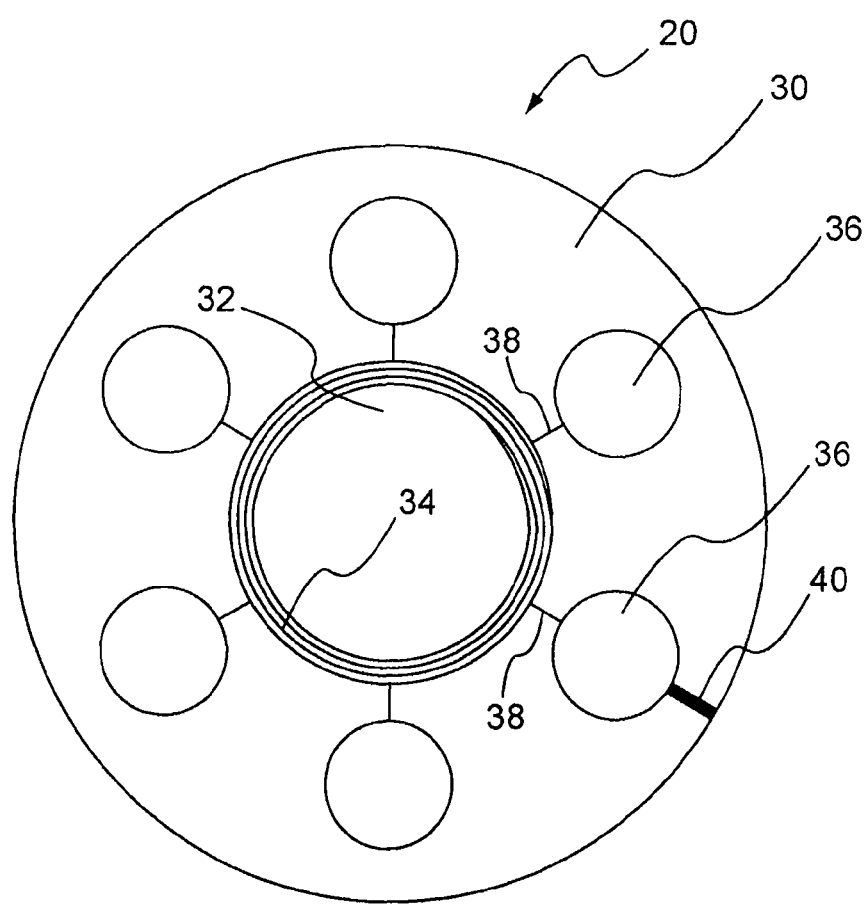
FIG. 2E is a top view of an alternative embodiment of a cap in accordance with an exemplary embodiment of the present invention.

With reference to FIG. 2E, in one embodiment, cap 20 is configured as a planar disk 30 with a center hole 32, wherein the center hole 32 includes an interface component 34 on its inner circumference surface. In an exemplary embodiment, the pitch of the saw tooth interface component is about 0.25 mm-0.5 mm. The planar disk 30 may also include any configuration for facilitating expansion of the disk 36 while sliding down wire 12. The configurations may include, for example, a cut 38 or a hole 36 in the planar disk 30. The planar disk may include multiple holes or cuts spaced over the planar surface. One or more of the additional holes 36 may also be connected to a cut 38 in the planar surface that extends to the center hole 32. One or more of the holes 36 may also be connected to a cut 40 in the planar surface that extends to the outside edge of the planar surface. In one embodiment, six additional holes 36 are evenly spaced around the planar surface with each hole 36 connected to a cut 38 which extends to the center hole, while one hole 36 also includes a cut 40 that extends to the outside edge of the planar surface.

The planar disk may also set inside a shallow cup device, wherein the circumference of the cup is slightly larger than the circumference of the planar ring in order to allow expansion of the ring. Moreover, a spring, or any other device suitably configured to apply pressure to cap 20, is placed between the planar ring and the cup device. In one embodiment, a bellville spring is used to apply pressure to the cap 20. The spring is configured to provide force on wire 12 after resorption. During the healing process, cartilage forms at the fracture and the cartilage compresses, so bone resorption typically occurs at the location of the fracture. When force on the lagwire is released due to bone resorption during healing, in one embodiment, cap 20 allows for auto tightening of the lagwire because micro-motions or vibrations will often cause cap interface device 22 to click down another notch on the inverse interface device of the wire 12.

Figure 2F:
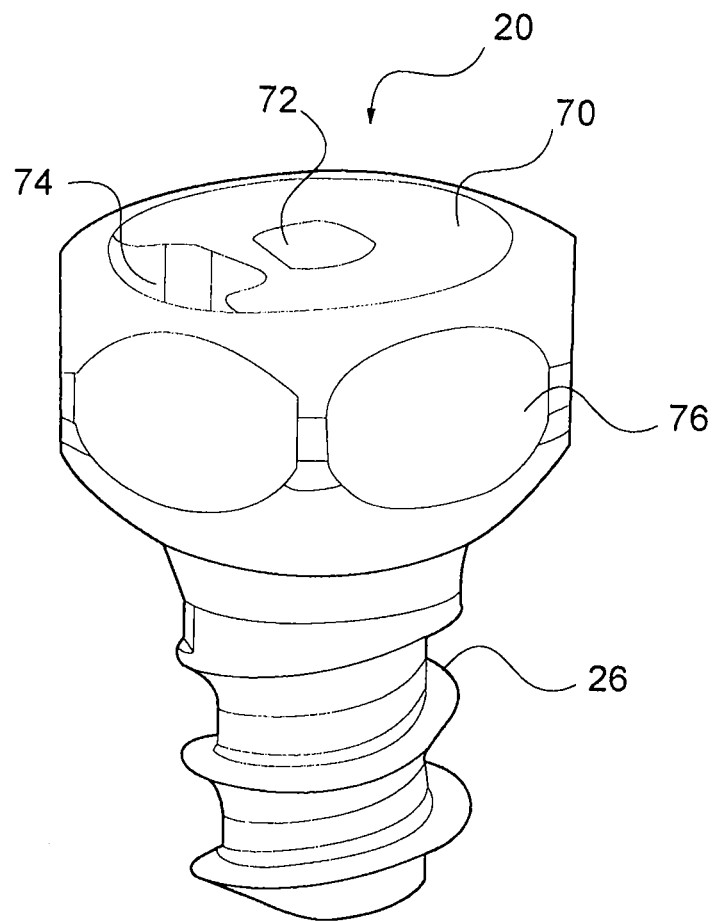
FIG. 2F is a perspective view of another embodiment of a cap in accordance with an exemplary embodiment of the present invention.
Figure 2G:
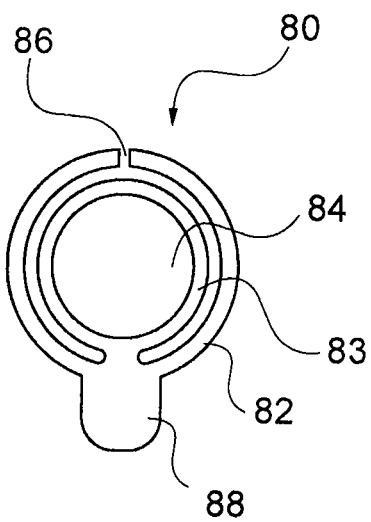
FIG. 2G is a top view of an exemplary spring in accordance with an exemplary embodiment of the present invention.

Another embodiment of a cap 20 is shown in FIG. 2F. As discussed above, cap 20 fits over one end of wire 12, such that cap 20 permits travel of cap 20 in one direction (e.g., distal travel with respect to the wire, toward the bone), but resists travel of cap 20 in the other direction (e.g., proximal travel with respect to the wire, away from the bone). In exemplary embodiments, cap 20 includes cutting threads 26, cover 70, a spring 80 and substantially flat surfaces 76 around the circumference of cap 20 to facilitate griping and/or turning cap 20. Cap 20 may be configured with a wider upper section which includes flat surfaces 76 around its circumference, and a tapered lower section with a gradually reducing diameter. Cutting threads 26 extend from the lower section. Cap 20 may include different thread configurations, lengths, diameters, pitches and the like to facilitate insertion into different types of bone or other structures (e.g., cortical bone, cancellous bone, etc).

Cover 70 may be integral with cap 20, or may be a separate component which is permanently or temporarily set in, or affixed to, cap 20. In one embodiment, cover 70 includes an opening 72 (e.g., in center of cover 70) which receives wire 12 and an inlet 74 which is configured to receive a component of extractor tool 90.

In one embodiment, tension spring 80 is set inside cap 20. In one embodiment, and with reference to FIG. 2G, tension spring 20 sits within cap 20 below cover 70; is circular; includes opening 84 (e.g., in center of circular ring) which receives wire 12; includes an outer ring 82 and an inner ring 83; includes a cut into, or non-connecting portion 86 of, outer ring 82 and/or inner ring 83; and/or includes a tab 88 which extends outward from outer ring 82. Outer ring 82 and an inner ring 83 may be one integrated ring, or two or more separate rings, which may not be connected, or may be connected in any manner.

At least a portion of inner ring 83 (or any portion of inner circumference of tension spring 80) provides greater friction against wire 12 one way (e.g., when the cap is pulled proximal, away from the bone). The friction is asserted against wire 12 because cover 70 impacts tab 88, so tab 88 forces tension spring 80 to flex, torque and/or tilt (e.g., 15 degrees) opening 84, thereby causing at least a portion of inner ring 83 to assert friction against at least a portion of wire 12. When cap 20 is pushed the other way (e.g., when the cap is pushed distal, toward the bone, using extractor 90), tab 88 is forced away from cover 70 and does not tilt, so it does not engage any surface, and the wire is able to translate, with minimal or no friction, through the central opening in the tension spring.

Figure 5A:
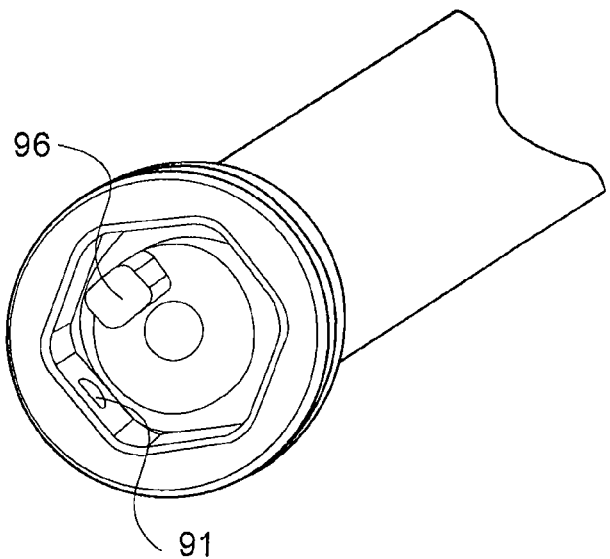
FIG. 5A is an exemplary head of the extractor of FIG. 5B in accordance with an exemplary embodiment of the present invention.
Figure 5B:
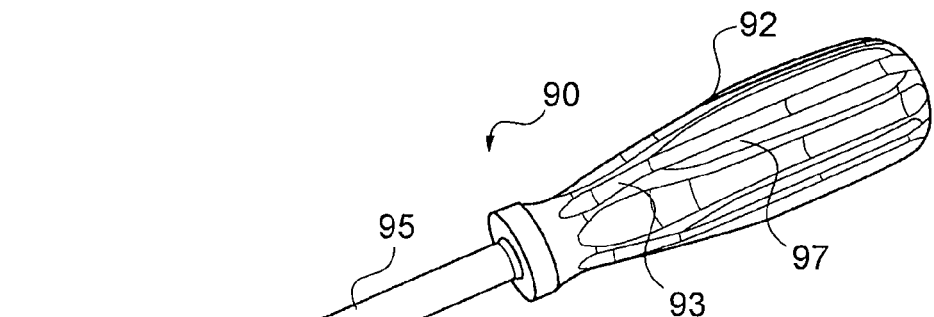
FIG. 5B is an exemplary extractor in accordance with an exemplary embodiment of the present invention.

Extractor/Driver 90, with reference to FIGS. 5A and 5B, includes any device suitably configured to insert and/or extract cap 20. In one embodiment, extractor 90 includes one or more ball bearings 91, shaft 95, shaft end 93, handle 92 which receives shaft end 93, tip sleeve 94, tip 96, and/or spring 97. Tip 96 may be the end of a long rod which extends upward into handle 92. Spring 97 applies pressure against the upper end of the rod that emanates from tip 96, thereby asserting a load against tip 96. Tip 96 is thus configured to be received into inlet 74 of cap 20 and the spring-load maintains tip 96 in inlet 74. Tip sleeve 94 is configured to receive cap 20 to also facilitate rotation and/or translation of cap 20. Tip 96 is mounted on a disc such that it allows tip sleeve 94 to more fully receive cap 20. The disc also rotates such that extractor 90 may rotate around cap 20, with minimal or no movement of tip 96. Ball bearings 91 are configured to facilitate rotation of tip sleeve 94 around outer surface of cap 20.

Figure 5C:
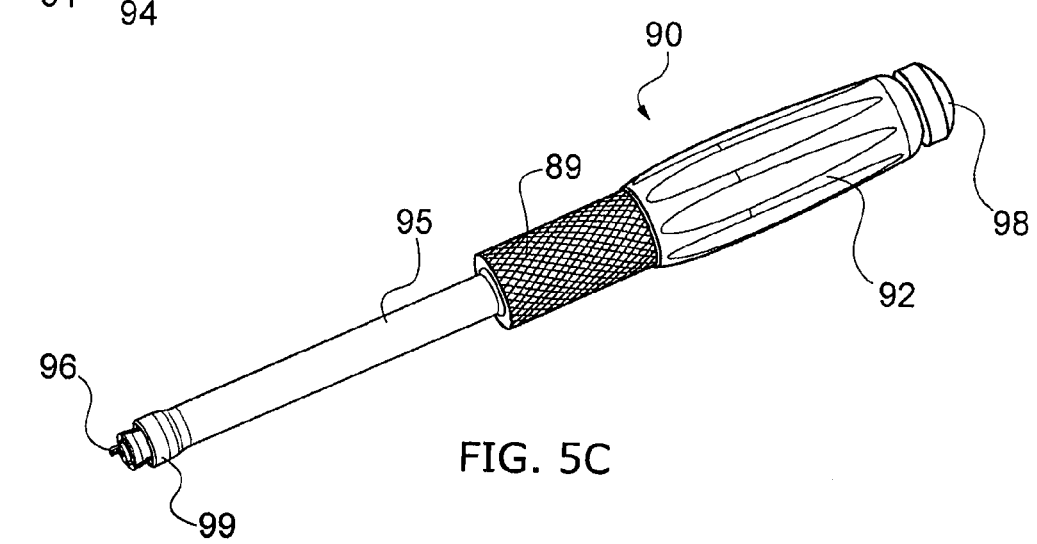
FIG. 5C is another embodiment of an exemplary extractor in accordance with an exemplary embodiment of the present invention.

Another embodiment of extractor/driver 90 is shown in FIG. 5C. In this alternative embodiment, the rod may have a first end which includes tip 96, and a second end 98 which may exit handle 92 such that the user may apply pressure to the second end 98 of the rod, thereby similarly applying pressure and a load against tip 96. Exit handle 92 also rotates such that it enables rotation of tip 96 which allows the user to rotate tip 96 until tip 96 mates with the inlet in cap 20. In another embodiment, collet sleeve 99 is attached to collet advancing handle 89. Collet advancing handle 89 includes a threaded inner surface which is configured to advance shaft 95, and thus, advance collet sleeve 99 forward over cap 20 to facilitate grasping of cap 20 for removal of cap 20.

Figure 3A:
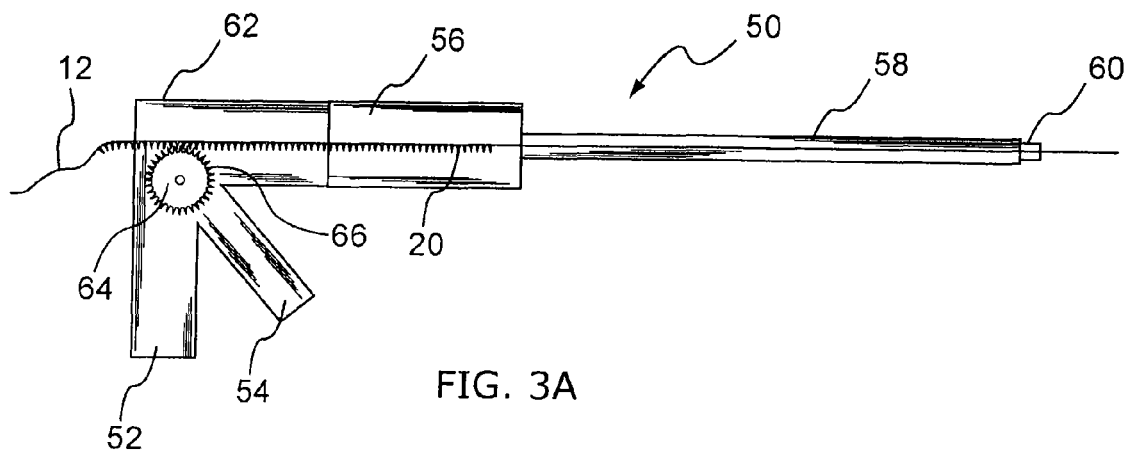
FIG. 3A is a tensioner in accordance with an exemplary embodiment of the present invention.

A tensioner 50 may also be used in conjunction with the present invention. With respect to FIG. 3A, tensioner 50 is any device suitably configured to insert a cap 20 into an object and/or provide tension to a wire 12. In one embodiment, tensioner 50 increases the pressure between the surfaces of pathology by providing force to a wire 12 while the head component 2 of wire 12 is fixed into a bone or far cortex. In an exemplary embodiment, tensioner 50 includes a handle 52 with a hand trigger 54, wherein the handle 52 supports a rotatable barrel 56 which mates with a cylindrical rod 58. Cylindrical rod 58 may be cannulated to receive wire 12 and/or have a driver 60 (e.g., hex, phillips, screw, allen and/or the like) at its distal end for mating with the tool attachment 10 of head component 2. The barrel 56 may be rotated manually or automatically in order to rotate the driver 60 into the object (e.g., bone or cortex). In one embodiment, tensioner 50 includes a means for exerting a force on wire 12, such as, for example, internal gears 64, wherein the gears 64 include an interface component 66 (e.g., saw tooth) which mate with the inverse sawtooth 20 on wire 12. By pivoting the hand trigger 54, the internal gears are rotated such that the gears cause wire 12 to translate out the back end 62 of the tensioner 50, thereby exerting force on wire 12 which is fixed at its distal end. The tensioner 50 may also include a gauge type device or any other device which is suitably configured to measure and/or display the tension exerted on wire 12.

Figure 3B:
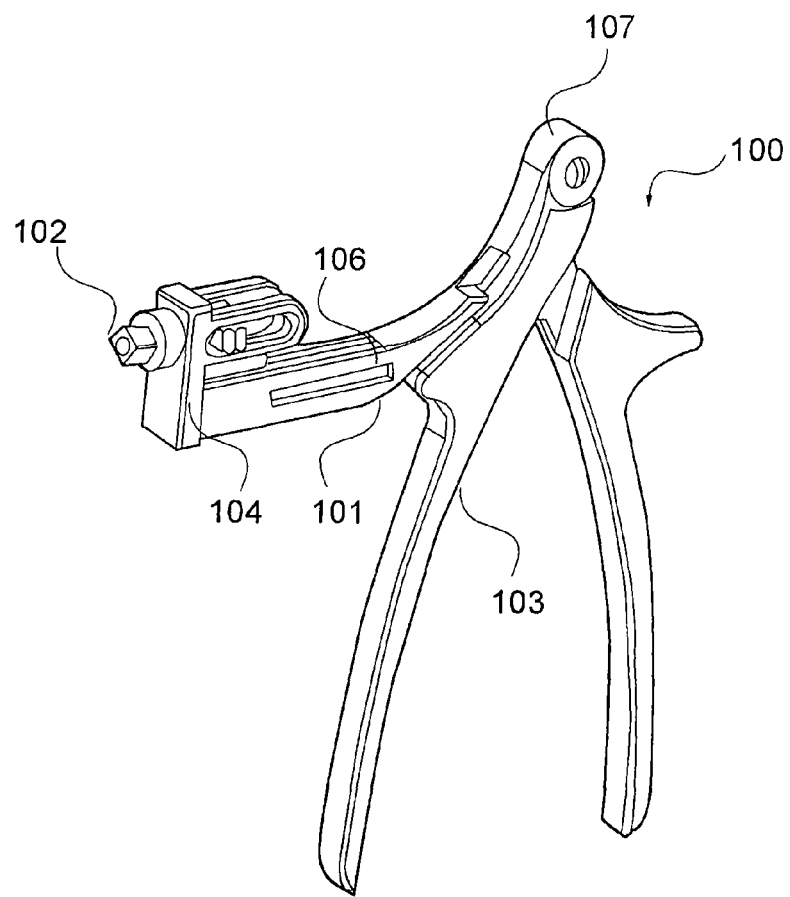
FIG. 3B is another embodiment of a tensioner in accordance with an exemplary embodiment of the present invention.

Another embodiment of a tensioner (e.g., tensioner 101) is shown in FIG. 3B. In one embodiment, tensioner 100 includes a base 101, a DVR connect component 102, a handle 103, a lock 104, and/or a spring link 106. Tensioner 100 is configured to accept multiple size wires and may include an indicator to show the amount of tension being applied. Tensioner 101 is also configured such that extractor 90 may clip into tensioner 101.

Figure 6:
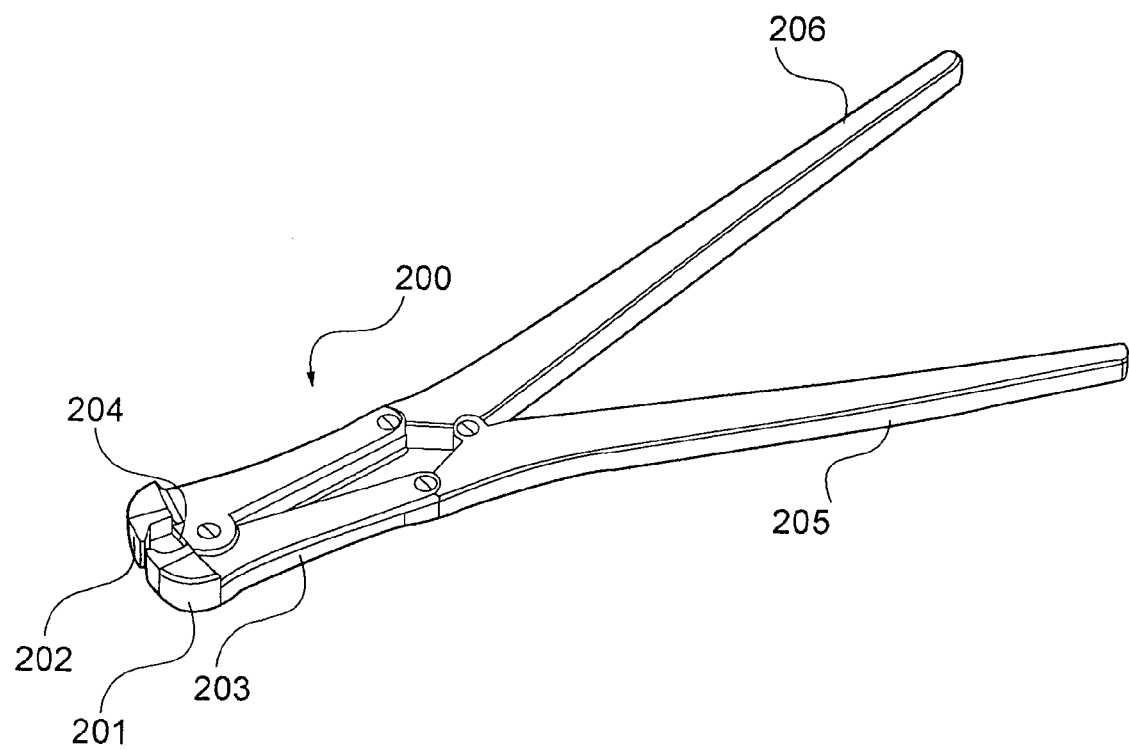
FIG. 6 is an exemplary cutter in accordance with an exemplary embodiment of the present invention.

After tensioning wire 12 to the desired tension, wire 12 may be cut, broken or shortened using any known device or method. With reference to FIG. 6, cutter 200 may be used. Cutter 200, in one embodiment, includes insert left 201, insert right 202, jaw left 203, jaw right 204, cutter left 205, and cutter right 206. Cutter 200 includes a cutting surface that extends beyond the main body of cutter 200 such that the wire may be cut from various angles.

The various components discussed herein can be suitably configured to perform the following method, wherein the steps can be performed in any order and any individual step is not necessary to the method. In an exemplary embodiment, a cannulated lagwire driver is suitably attached to a surgical drill, such that the drill allows for automatic rotation of the driver. The wire 12 of lagwire system 1 is placed into the channel of the driver such that the end of the driver encompasses or is received into driver head 10 of head component 2, thereby allowing wire 12 to be drilled into the bone. In one embodiment, head component 2 is configured with a hex head as the driver head 10 such that the driver suitably mates to the hex head. The head component 2 and wire 12 are then drilled into the bone to a desired depth using the automatic surgical drill (or any other manual or automatic device for rotating head component 2). Specifically, drill tip 4 of head component 2 facilitates the drilling of a pilot hole, wherein the proximal cutting threads 6 tap the bone for threading the inner surface of the hole, then the proximal mating threads 8 rotationally mate with the newly created threaded surface, thereby temporarily attaching the head component 2 into the cortex of the bone.

After attaching the head component 2 to the bone, the surgical drill is removed and a cap 20 is threaded onto the proximal end 14 of wire 12. Cap 20 is then translated distally along wire 12 until cap 20 contacts the bone or other desired pathology. In one embodiment, a lagwire tensioner is used to exert tension on the lagwire. In another embodiment, a lagwire tensioner 50 may be used to force or seat cap 20 into the bone surface or any other desired position. The hex head 60 of the tensioner 50 may be used to screw cap 20 into the bone surface. In another embodiment, the lagwire tensioner 50 exerts tension on the lagwire 12 up to a desired tension which may be read from a gauge communicating with the tensioner.

After positioning the lagwire device 1 and applying the appropriate amount of tension, in one embodiment, the excess wire 12 may be suitably removed by, for example, a wire cutter or any other suitable device. In another embodiment, a crimp type device may be placed on wire 12 to also help maintain tension. The crimp may include a clamp type device, bending the existing wire 12, screwing a nut onto the end of wire 12 and/or the like. The crimp may be placed on wire 12 after cap 20 is set in place, for example, in order to crimp other end pieces together. The tensioner 50 may also be used to reverse screw cap 20 in order to remove a wire 12 out of the bone. Moreover, in a situation where head component 2 strips out of the bone (for example, when the bone is of poor quality), the present invention allows the lagwire to be pushed through the opposite side of the bone and through the skin such that the head component 2 of wire 12 can be suitably removed (e.g., cut off) and a cap 20 can be placed onto that end of the lagwire, thereby resulting in better purchase (e.g., quality of fixation) of the bone.

Figure 4A:
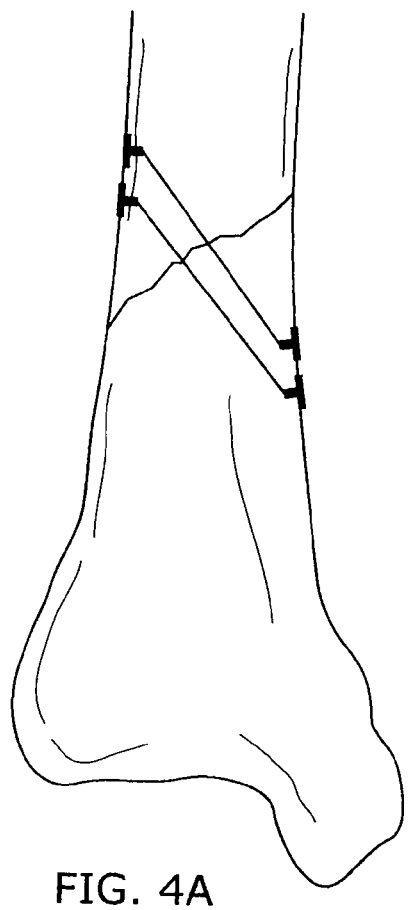
FIG. 4A is a fixation of a bone fracture in accordance with an exemplary embodiment of the present invention.
Figure 4B:
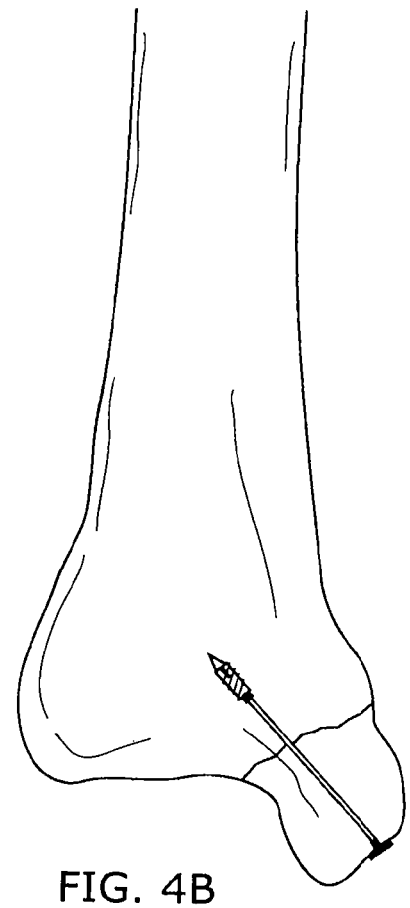
FIGS. 4B-4D are fixations of fractures of a certain portions of a bone in accordance with an exemplary embodiment of the present invention.
Figure 4C:
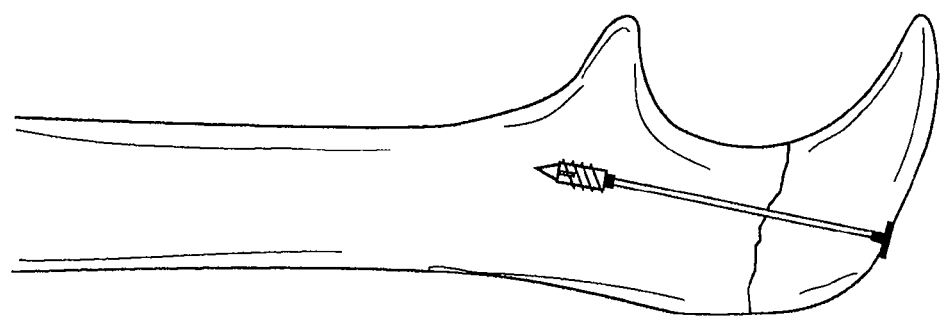
Figure 4D:
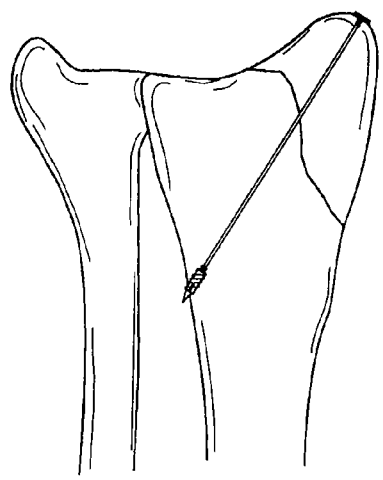
Figure 4E:
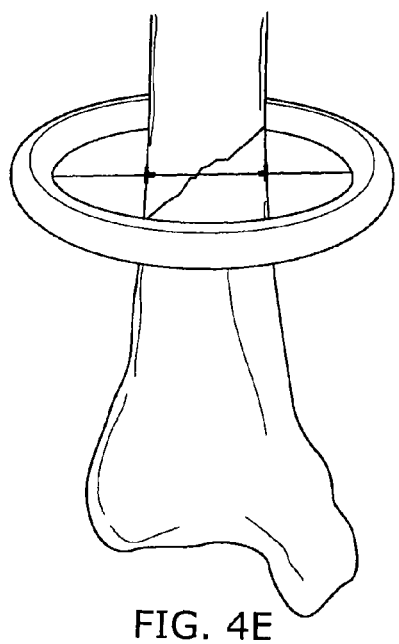
FIG. 4E is a fixation of a bone fracture by inserting the lagwire through the entire limb to facilitate attaching an external fixation device to the limb in accordance with an exemplary embodiment of the present invention.
Figure 4F:
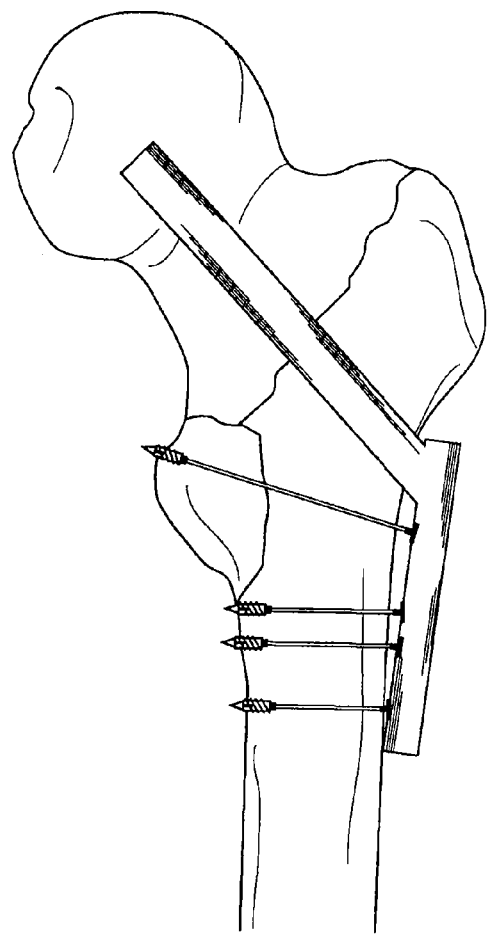
FIGS. 4F-4G is a fixation of a bone fracture by inserting the lagwire through the entire limb to facilitate holding a plate to the bone to help fix certain types of fractures in accordance with an exemplary embodiment of the present invention.
Figure 4G:
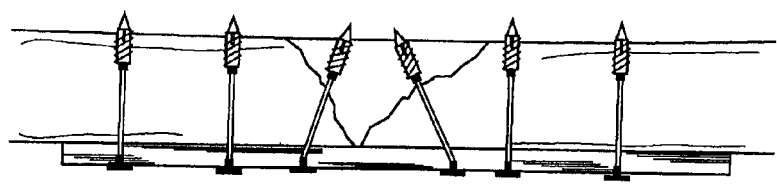

With respect to FIGS. 4A-4G, the lagwire system discussed herein can be used for the fixation of various types of bone fractures. FIG. 4A shows the use of the present invention for an exemplary fixation of a bone fracture or break. FIGS. 4B-4D show the use of the present invention for an exemplary fixation of fractures of certain portions of bones. Moreover, as shown in exemplary FIGS. 4F and 4G, the lagwire system 1 may also be used in a similar manner discussed herein in order to assist in holding a plate to the bone to help fix certain types of fractures. In other types of fractures, the lagwire may be placed through an entire limb to, for example, attach an external fixation device to the limb as shown in exemplary FIG. 4E.

Figure 4H:
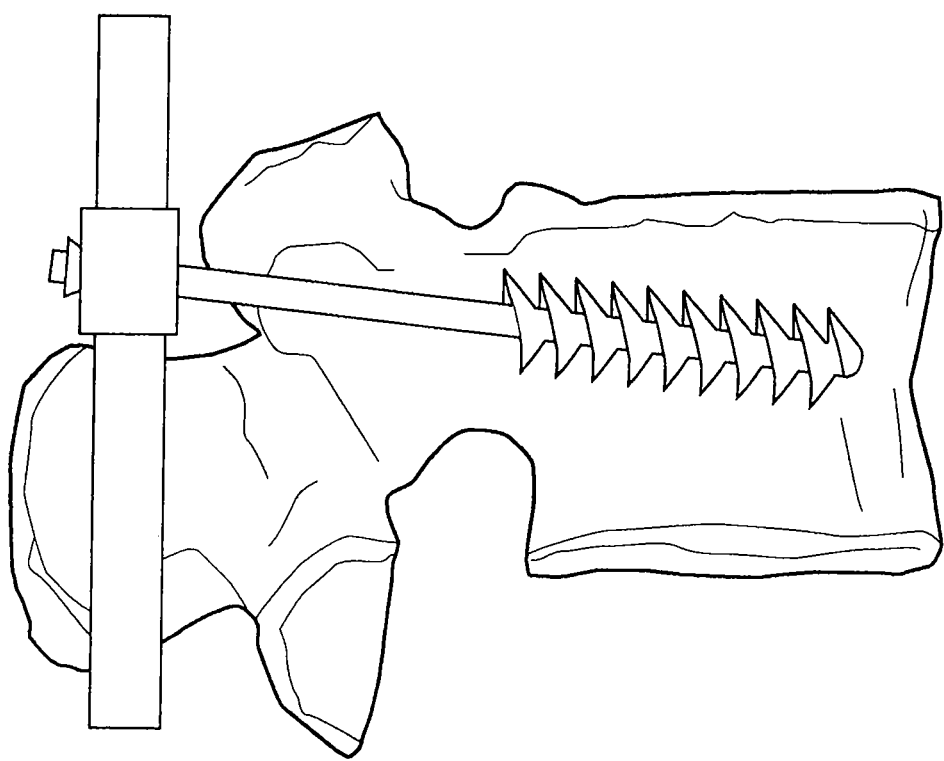
FIG. 4H is a fixation of a spinal injury in accordance with an exemplary embodiment of the present invention.

FIG. 4H shows a fixation of a vertebrae in accordance with an exemplary embodiment of the present invention. The screw is inserted into the vertebrae, then a cap is fitted onto the end of the wire. The cap is specially constructed such that the cap attaches to a rod. The rod may extend along various vertebrae such that the lagwires may extend from various vertebrae and all connect to the same rod. Another screw and lagwire may be inserted into the other side of the vertebrae such that the wire extends from the other side of the vertebrae and its cap connects to a second rod on the other side of the vertebrae for additional stability.

As described herein, the system and method of the present invention provides a device which is self-drilling, self-tapping and can be inserted under power. The invention also facilitates reducing and fixing fractures in one step. As such, the invention substantially expedites the process for fixation of bone fractures which is, of course, critical during trauma situations in order to stabilize a patient or to minimize the amount of time the patient is on the operating table or under anesthesia. In contrast to typical prior art screws wherein a gliding hole in the near cortex simply guides the screw, the present invention provides the ability for two sides of cortex bone screw fixation. Moreover, because of the strength of the attachment to the bone, the invention enables sufficient fixation even in poor quality bone material. Furthermore, wherein the prior art systems often require the use of cannulated screws in order to utilize a guidewire for placement, the present invention does not require the use of cannulated screws. Because the lagwire includes a tip 4 which creates a pilot hole, taps the bone for threads and fixes the threads into the bone, the system and method minimizes the possibility of inaccurate placement into the distal cortex or missing the distal hole.

In prior art systems, the physician typically cuts a relatively large opening in the skin in order to locate the bone segments, pull the bone segments into alignment, then place the screw into the bones. In the present invention, the system facilitates the percutaneous technique by allowing the physician to cut a minor incision into the skin for the head component, insert the head component, then pull the bones together with wire 12 and set the cap, all without large incisions or additional incisions.

Another embodiment for a bone fixation device includes a collapsing bone fixation device which is suitably configured to collapse in association with a fracture collapse to minimize or prevent the device from protruding beyond the bone. In an exemplary embodiment, the bone fixation device also includes an internal (i.e., minimal or no contact with the bone) compression device 140 to maintain compression across the fracture during fracture collapse (e.g., weight bearing by the patient).

Figure 7:
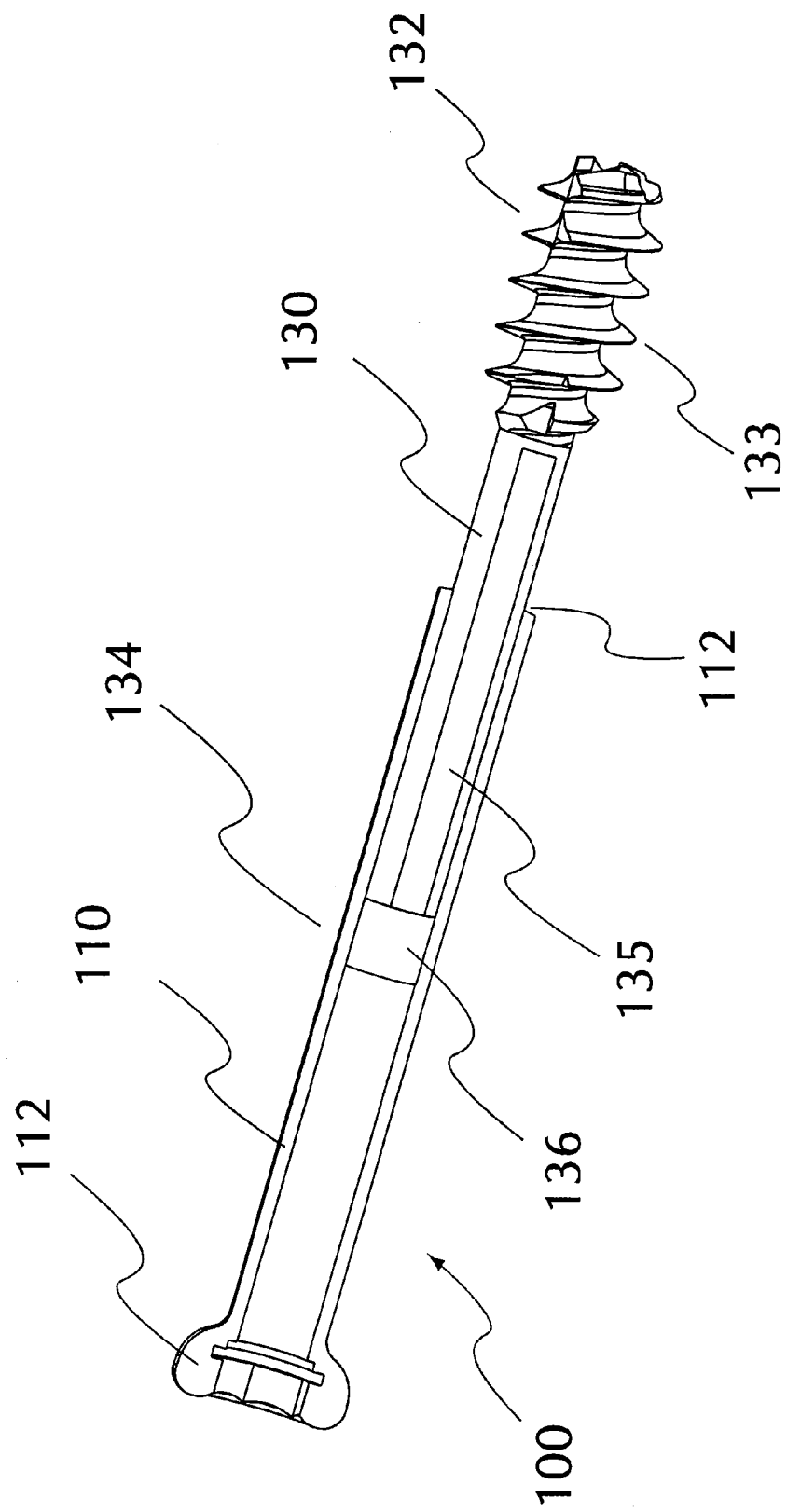
FIG. 7 is a cannulated screw having a sleeve and a threaded shaft in accordance with an exemplary embodiment of the present invention.

With respect to FIG. 7, an exemplary embodiment includes an improved screw 100 having a sleeve 110 and a shaft 130. In one embodiment, no additional elements exist between sleeve 110 and shaft 130, but in other embodiments (as discussed below in more detail and in FIGS. 8 and 9), a compressive device 140 (e.g. spring) is located between sleeve 110 and shaft 130. In an exemplary embodiment, each of the elements sleeve 110, shaft 130, and compressive device 140 are cannulated.

In one embodiment, with respect to FIG. 7, shaft 130 includes a first end 132 having a gripping device 133 and a second end 134. Gripping device 133 may include any structure and configuration for enabling shaft to enter and attach to an object. In one embodiment, gripping device includes a threaded surface thereon. The threaded surface may include cutting threads, mating threads, barbs, ribbed surface or any other surface configured to retain shaft 130 into an object. In an exemplary embodiment, gripping device 133 is about 0.63 inches in length with a pitch of about 9 threads per inch.

In one embodiment, shaft 130 is generally cylindrical, but includes one or more flat outer surfaces 135. In a particular embodiment, second end 134 includes two rectangular flat, opposing surfaces which extend over the entire length of shaft 130, but terminate prior to gripping device 133. In an exemplary embodiment, the flat surfaces of shaft 130 are each about 1.25 inches in length.

In one embodiment, second end 134 of shaft 130 is configured to restrict shaft 130 from translating beyond a particular location. In an exemplary embodiment, end cap 136 is located on or near second end 134, and is formed in a cylindrical configuration such that end cap 136 freely translates within the cylindrical portion of sleeve 110, but end cap 136 stops the translation of shaft 130, when end cap 136 impacts the flat inner surface of sleeve 110. End cap 136 limits the expansion of compressive device 140 to a certain point, so continued compression can be applied against the fracture. End cap 136 may be integral with shaft 130, welded onto shaft 130, or otherwise affixed to shaft 130.

With continued reference to FIG. 7, a wider diameter head 112 is located at the first end of sleeve 110. An exemplary diameter of head 112 is about 0.387 inches. Head 112 includes a recessed portion for receiving the hex head of a tool. One skilled in the art will appreciate that head 112 may be any configuration suitably configured to receive any suitable working tool. The recessed portion is about 0.10 inches in depth and about 0.198 inches wide. Head 112 (or any other portion of sleeve 110) may also include a ledge 114 for retaining compressive device 140 within sleeve 110. Cap 20 (discussed above in other embodiments) may be configured as sleeve 110 (or barrel) and any components of cap 20 may be incorporated into bone screw 100.

A second end of sleeve 110 includes an opening 112 which receives shaft 130 such that shaft 130 is able to at least partially move within sleeve 110, with minimal or no movement of sleeve 110. As discussed above, in one embodiment, the inner surface of sleeve 110 is generally cylindrical, but the inside surface also includes two rectangular flat, opposing surfaces which extend along a portion of the length of sleeve 110. In an exemplary embodiment, the overall sleeve 110 is about 1.85 inches long, about 0.22 inches outer diameter, and about 0.161 inner diameter with a reduced distance between the flat surfaces of about 0.14 inches with the flat surfaces of sleeve 110 being each about 0.545 inches in length.

Figure 8:
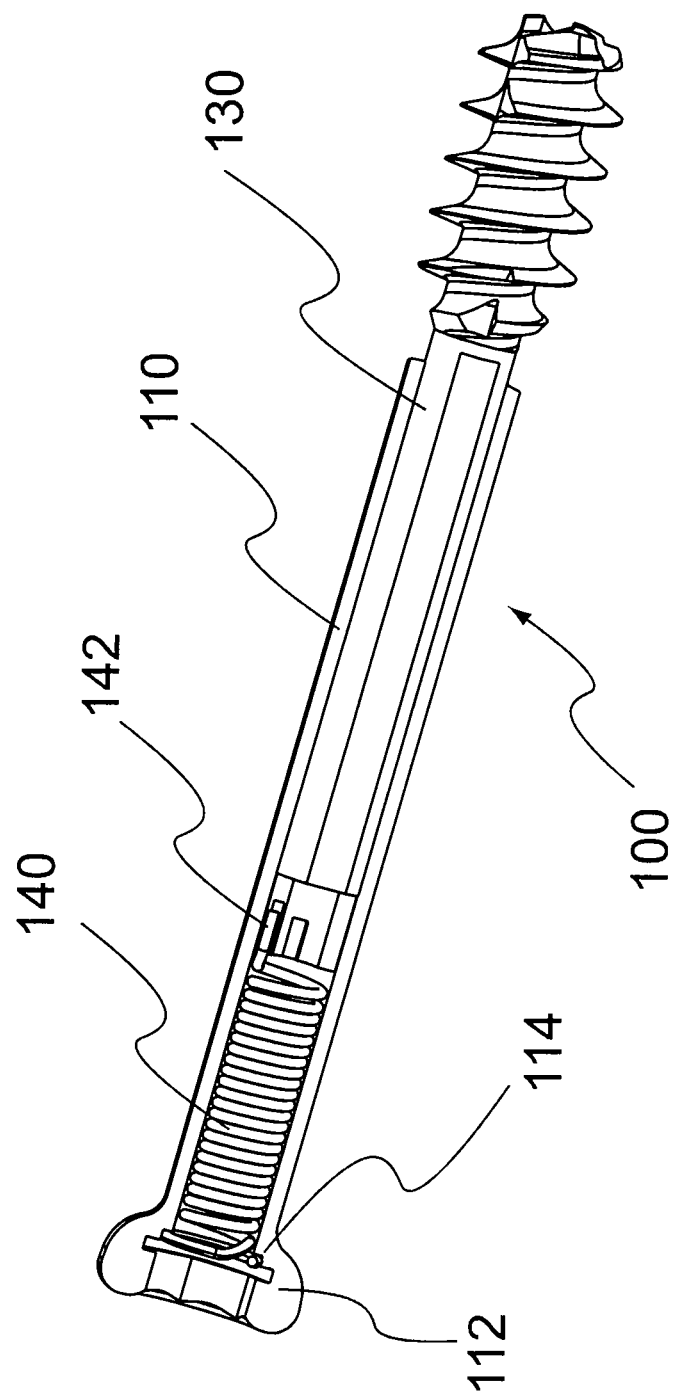
FIG. 8 is a cannulated screw having a sleeve, a compressive device and a threaded shaft and shown prior to extending the compressive device, in accordance with an exemplary embodiment of the present invention.

In one embodiment, and with respect to FIG. 8, a compressive device 140 exists between sleeve 110 and shaft 130 such that compressive device 140 exerts a force directly or indirectly against shaft 130. Compressive device 140 may include, for example, a spring or any other element which exerts a force and/or bears a load. In one embodiment, compressive device 140 is located inside sleeve 110 (as discussed above). In a particular embodiment, compressive device 140 is a spring having about 10 mm of extension. As such, compressive device 140 allows about 10 mm of compression before sleeve head 112 is no longer held against the cortex.

Compressive device 140 may be suitably affixed to sleeve 110 and shaft 130 in any manner known in the art. In an exemplary embodiment, first end of compressive device 140 includes a larger diameter coil which sits upon ledge 114 of head 112, thereby restricting or minimizing translation of compressive device 140 within sleeve 110. The larger diameter coil may also be further retained by a C-clip or laser welding to sleeve 110 (e.g., at any location within the first end).

Second end of compressive device 140 may include a tang 142. Tang 142 may extend longitudinally from the perimeter of the end coil. Tang 142 may be crimped into a hole in shaft 130, laser welded to the end of shaft 130 and/or any other means for attaching tang 142 to shaft 130. In other embodiments, shaft 130 may abut compressive device 140, compressive device 140 may receive shaft 130 within its coils, or compressive device 140 may abut a component attached to shaft 130. For example, compressive device 140 may be a separate component suitably joined (e.g., welded, glued, molded) to shaft 130 and/or end cap 136.

Locating compressive device 140 inside sleeve 110 is significantly advantageous because the compressive device is fully or partially protected from bone growth over and between the coils which may limit or destroy the functionality of the spring. Similarly, a re-absorbable material is not needed to be inserted between the coils in order to delay the compressive action of the spring. In other words, upon insertion, compressive device 140 is able to provide immediate and subsequent compression. Moreover, because shaft 130 and sleeve 110 rotate along with compressive device 140, bone screw device 100 may be inserted or removed with minimal or no torque or unraveling of compressive device 140.

Figure 10:
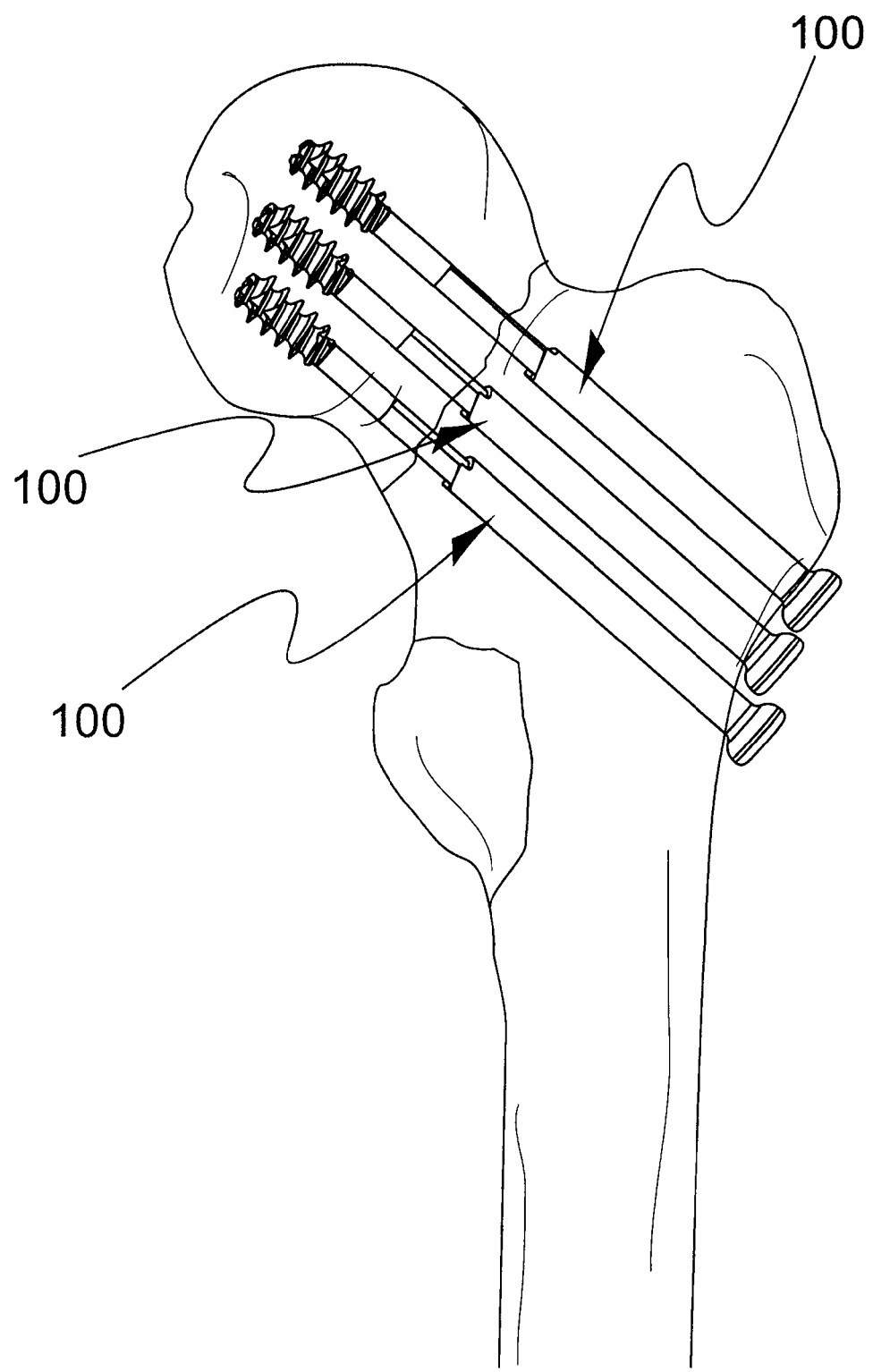
FIG. 10 shows multiple cannulated screws providing rotational stability to a fracture, in accordance with an exemplary embodiment of the present invention.

Multiple bone screws 100 of the present invention may also be used for rotational stability. For example, as set forth in FIG. 10, more than one bone screw (e.g., three) are used to maintain compression and provide rotational stability in a fracture within the head of the femur bone.

Figure 11:
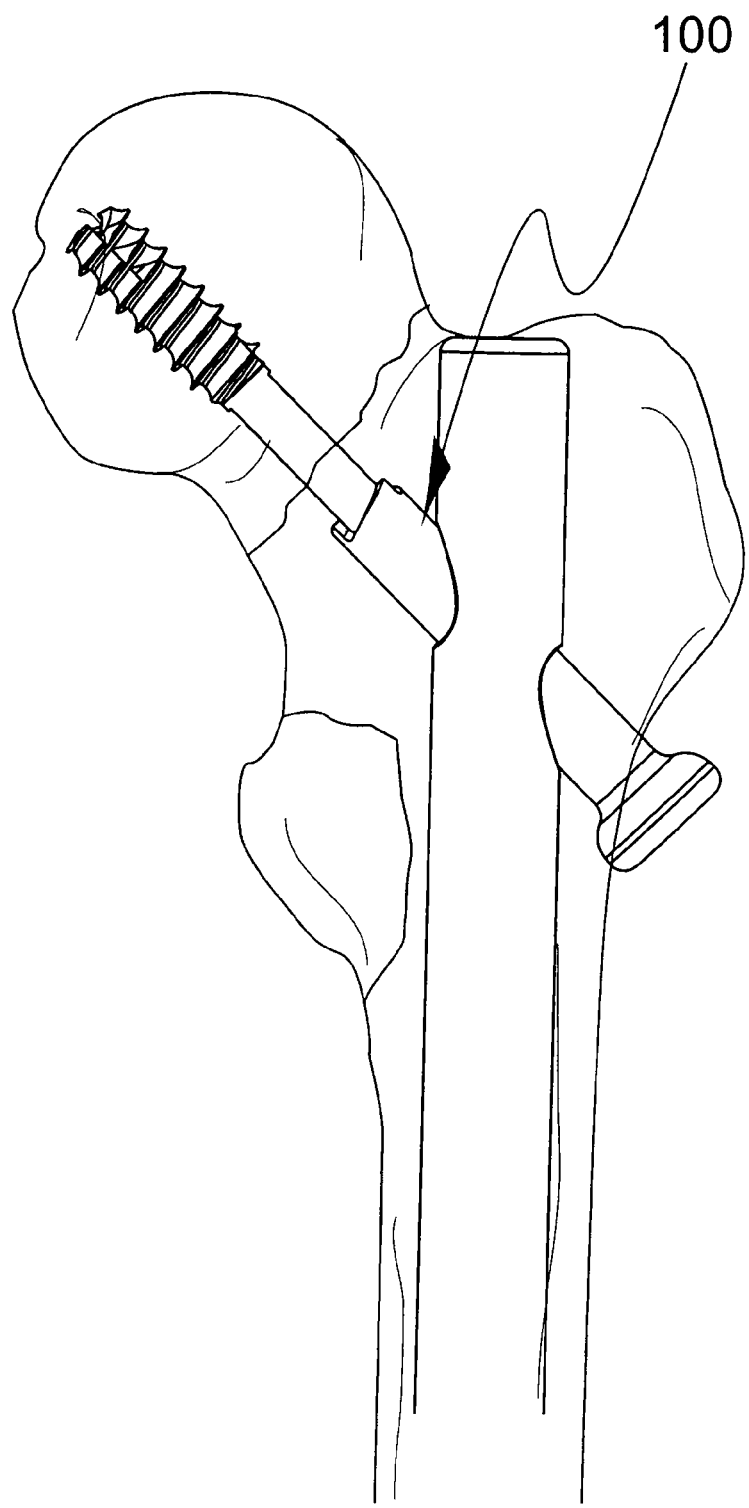
FIG. 11 shows a cannulated screw received through an intermedulary rod, in accordance with an exemplary embodiment of the present invention.

Bone screw 100 of the present invention may be used in place of any existing bone screw, or any existing component of a product that performs a similar function as a bone screw. With respect to FIG. 11, bone screw 100 is used in association with an intermedulary rod for additional support and stability.

Figure 12:
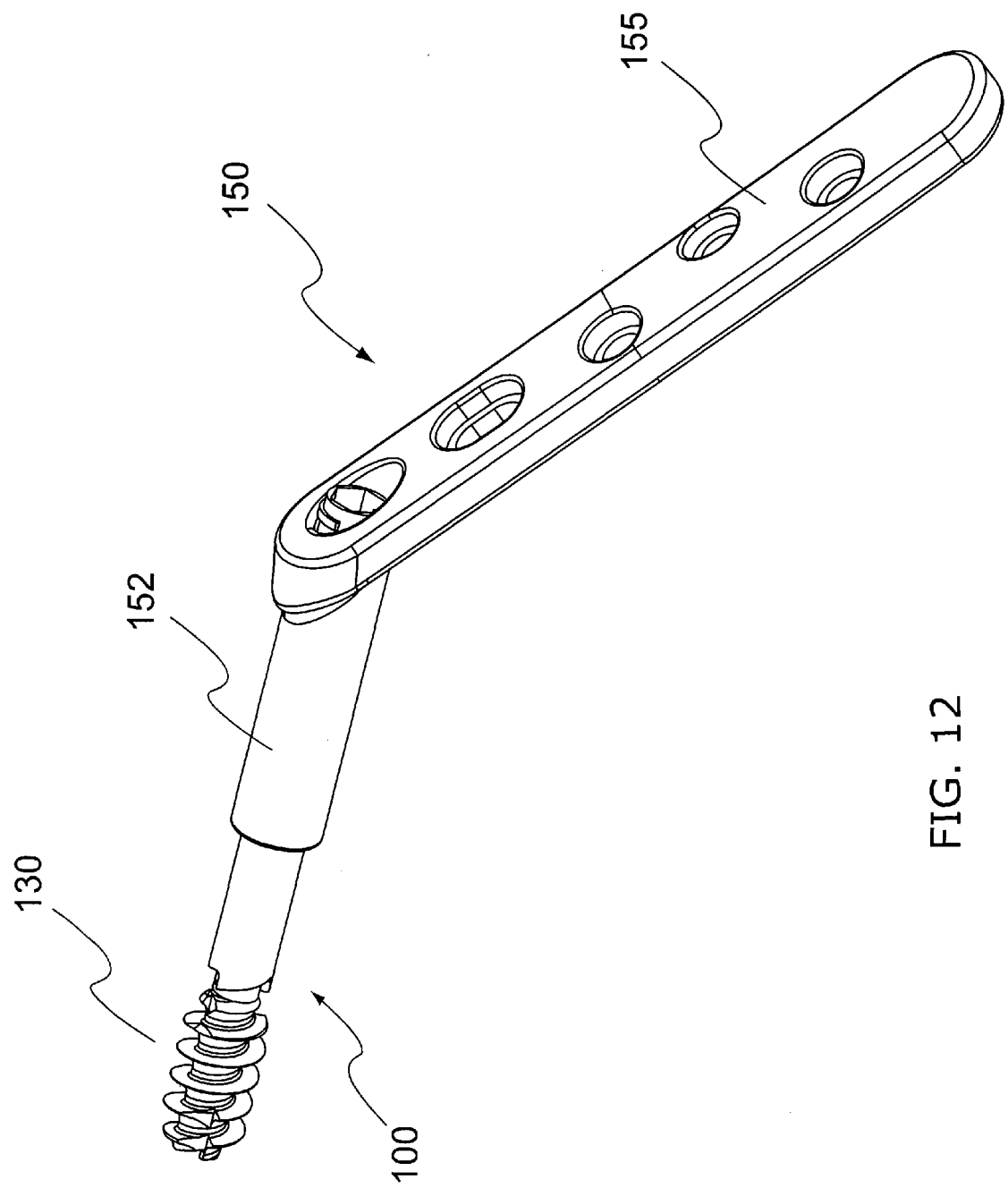
FIG. 12 shows a cannulated screw with a sleeve and a barrel as part of a hip screw plate system, in accordance with an exemplary embodiment of the present invention.

With respect to FIG. 12, bone screw 100 is incorporated into a compression/dynamic hip screw system 150 which may be used on, for example, a proximal femur fracture. An exemplary hip screw system 150 may include any combination of the various compression hip screw plates and nails manufactured by Smith & Nephew. In one embodiment, bone screw 100 is received into barrel 152 of hip screw system 150 in place of the standard bone screw which is typically received into barrel 152. Barrel 152 may or may not include an additional compression device 140. In another embodiment, barrel 152 may act as a second sleeve 110, thereby adding to the available translation of shaft 130. In other words, shaft 130 translates within sleeve 110, and sleeve 110 itself may translate within barrel 152 before hip screw system 150 protrudes from the bone. In a further embodiment, sleeve 110 is affixed directly to plate 155, so a barrel is not needed.

Hip screw system 150 (with standard plate 155 and cortical bone screws) is inserted as is known in the art, and the features of the present invention incorporated into hip screw system 150 provide additional benefits by minimizing or preventing the device from protruding beyond the bone, and by maintaining an additional amount of compression across the fracture during fracture collapse. A T-Handle may be used to rotate bone screw 100 into the bone. One skilled in the art will appreciate that bone screw 100 may replace or supplement any of the screws (e.g., cortical bone screws, medial fragment screws and/or main bone screw) typically used in association with hip screw system 150.

Figure 13:
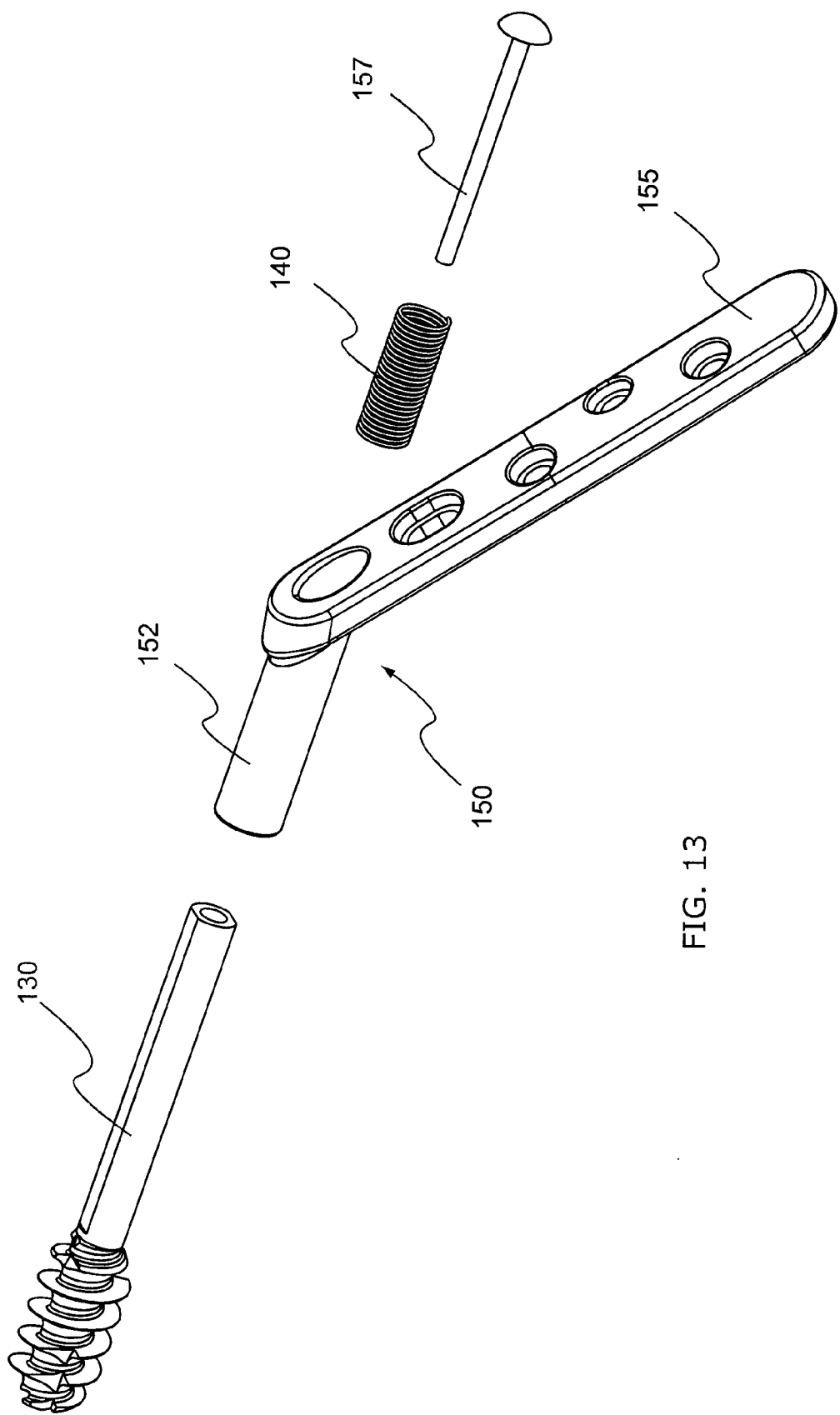
FIG. 13 shows another embodiment of a cannulated screw wherein the barrel functions as the sleeve, as part of a hip screw plate system, in accordance with an exemplary embodiment of the present invention.

FIG. 13 shows another embodiment of hip screw system 150, wherein shaft 130 is received directly into barrel 152 of existing hip screw system 150, without the need for a separate sleeve 110. A standard barrel 152 may be used or a longer opening formed within barrel 152 to allow shaft 130 greater translation within barrel 152. Barrel 152 may also include any of the features and functions described above with respect to sleeve 110. For example, barrel 152 may include one or more flat inner portions to complement flat portion 135 of shaft 130, a ledge 114 to hold a wider diameter spring, etc. Any of the hip screw systems may or may not incorporate a compressive device 140 inside sleeve 110 or barrel 152. Without compressive device 140, barrel 152 and/or sleeve 110 is still configured to allow shaft 130 to collapse within barrel 152 and/or sleeve 110, as discussed above.

Compression screw 157 is inserted through plate 155, through barrel 152 and into shaft 130. Upon rotating or translating compression screw 157 through barrel 152, the head of compression screw 157 engages (or abuts) a recessed portion of plate 155 and/or a recessed portion of barrel 152. Upon continuing to rotate compression screw 157, shaft 130 is "pulled" back into barrel 152, thereby causing further compression. In another embodiment, compression screw 157 is also received through compression device 140 which itself resides in barrel 152 and/or sleeve 110. Upon receiving a weight bearing load, hip screw system 150 allows shaft 130 to translate with minimal or no protrusion of hip screw system 150 beyond the bone, and also, maintaining an additional amount of compression across the fracture during fracture collapse.

Figure 9:
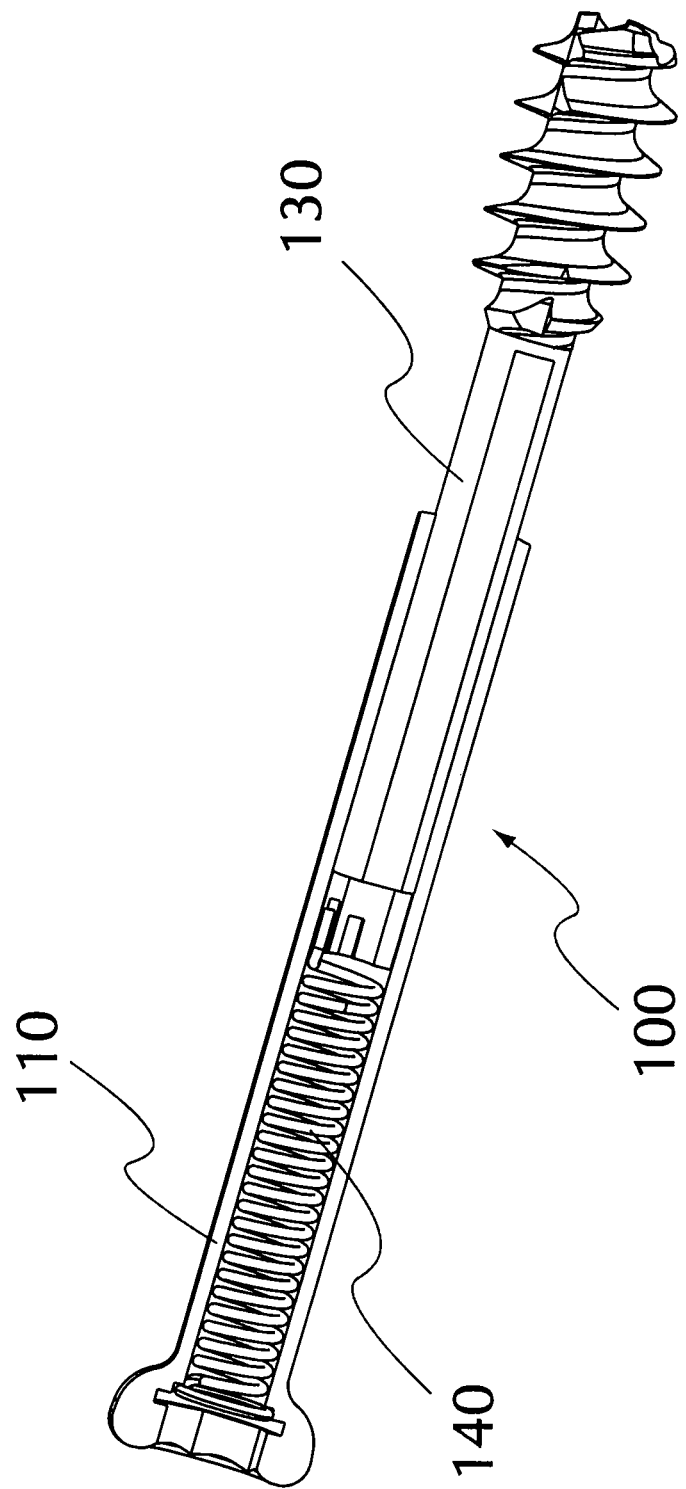
FIG. 9 is a cannulated screw having a sleeve, a compressive device and a threaded shaft and shown after extending the compressive device, in accordance with an exemplary embodiment of the present invention.

Having described exemplary components of the invention, exemplary methods for inserting bone screw 100 will now be described. An exemplary method for inserting bone screw 100 comprises drilling a bore hole into the two objects (e.g., two pieces of the fractured bone) which are to be compressed together. A guide rod is inserted into the bore hole, then cannulated bone screw 100 is inserted over the guide rod. Head 112 of bone screw 100 is then rotated (e.g. using a drill, hex head driver, or other suitable device) into and through the proximal bone fragment. Head 132 of shaft 130 then enters the distal bone fragment. When sleeve 110 impacts or sits flush against the surface of the proximal bone fragment (or against a plate placed over the bone fragment), head 112 of sleeve 110 continues to rotate, but sleeve 110 no longer translates into the bone. However, the rotation of sleeve 110 continues to advance shaft 130 further into the distal bone fragment because threads of gripping device 133 moves shaft 130 forward. Such continued translation and penetration of shaft 130 into the distal bone fragment also extends compressive device 140 (as best shown in FIG. 9). In other words, the continued advance of shaft 130 causes compressive device 140 to stretch beyond its relaxed condition. After the bone screw is appropriately inserted, the guide rods are removed.

One skilled in the art will appreciate that shaft 130 may penetrate into the distal bone fragment any desired partial or full distance, and thus, extend compressive device 140 to any desired partial or full extension/force. One skilled in the art will appreciate that any "rotational insertion" discussed herein may alternatively or additionally include other means for insertion such as, for example, a direct translation using a hammer to force the shaft and/or sleeve into the bone.

After insertion of bone screw 100, compressive device 140 exerts force against sleeve 110 and shaft 130, thereby forcing the components toward one another. Such force helps to maintain the compressive load at the union of the fracture. As additional compression is exerted on the load in a fracture collapse (e.g., from weight bearing), the bone fragments are compressed closer together, so force may be reduced. However, the present invention collapses in association with the fracture collapse to substantially minimize or prevent sleeve head 112 of bone screw 100 from protruding beyond the bone. In other words, sleeve head 112 is substantially maintained against the lateral cortex, while compressive device 140 maintains compression across the fracture during fracture collapse. That is, as the bone fragments undergo stress relaxation, bone screw 100 similarly relaxes, while continuing to hold the fragments together. As such, bone screw 100 continues to accommodate the stress relaxation of the bone fragments until the fracture therebetween has significantly or completely healed.

As discussed above, in one embodiment, compressive device 140 is a spring having about 10 mm of extension. As such, the spring allows about 10 mm of compression before shaft 130 impacts sleeve 110 so that sleeve head 112 is forced away from the cortex. Sleeve head 112 may be maintained against the lateral cortex until a sufficient amount of force no longer exists within compressive device 140, then bone screw 100 may simply act as a traditional bone screw.

The present invention is described herein in connection with the fixation of bone fractures; however, one skilled in the art will appreciate that the lagwire or bone screw system and method described herein may also be used for changing, maintaining, reducing or expanding the distance between objects or surfaces, compressing objects together or providing pressure to surfaces. For example, the present invention may be used to repair wood products, tree limb damage, breaks in supports or columns, cracks in sculptures or buildings, fractures in sections of concrete or other building materials, cracks or breaks in car parts and/or the like.

In the foregoing specification, the invention has been described with reference to specific embodiments. Various modifications and changes can be made, however, without departing from the scope of the present invention as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the invention. The scope of the invention is accordingly to be limited by nothing other than the appended claims, in which reference to an element in the singular is not intended to mean "one and only one" unless explicitly so stated, but rather "one or more." Moreover, where a phrase similar to 'at least one of A, B, and C' is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. All structural, chemical, and functional equivalents to the elements of the above-described exemplary embodiments that are known to those of ordinary skill in the art are expressly incorporated herein by reference and are intended to be encompassed by the present claims. Further, a list of elements does not include only those elements but may include other elements not expressly listed or inherent to such process, method, article, or apparatus.

The invention claimed is:

1. A system for maintaining a compressive load in a fracture between a first bone fragment and a second bone fragment, said system comprising a sleeve, a shaft, and a compression device, wherein said shaft, said sleeve, and said compression device are assembled prior to insertion into said first bone or said second bone fragments, wherein said shaft is reciprocally received within said sleeve, wherein a proximal end of said shaft remains between a distal end of said sleeve and a proximal end of said sleeve, wherein said compression device is located within said sleeve, and said compression device is engaged between a proximal end of said shaft and a proximal end of said sleeve, wherein said sleeve is retained within said first bone fragment, wherein said shaft is retained within said second bone fragment such that said sleeve and said shaft are configured to gradually collapse along with a collapse of said fracture; wherein said system is cannulated along its entire length; wherein said proximal end of said sleeve comprises a recessed region comprising a ledge; wherein said compression device comprises a helical coil having one end abutting said ledge and a second end fixedly attached to said proximal end of said shaft; wherein said shaft and said sleeve rotate together by means of mating longitudinally extending flat surfaces on each of said sleeve and said shaft.

2. The system of claim 1, wherein said sleeve is configured to be substantially maintained within said first bone fragment during said collapse of said fracture.

3. The system of claim 1, wherein said system acts as a traditional bone screw when said shaft collapses into and abuts a proximal end of said sleeve.

4. A system for maintaining a compressive load in a fracture between a first bone fragment and a second bone fragment, said system comprising:
a shaft comprising a distal shaft end and a proximal shaft end, wherein said distal shaft end is configured to be retained within said second bone fragment;
an endcap attached to said proximal shaft end;
a sleeve comprising a proximal sleeve end and a distal sleeve end, wherein said sleeve is configured to receive said proximal shaft end such that said shaft and said sleeve are permitted to travel longitudinally relative to one another, wherein said end cap is configured to limit said longitudinal travel between said sleeve and said shaft, said sleeve is configured to be retained within said first bone fragment, such that said sleeve and said shaft are configured to gradually collapse along with a collapse of said fracture;
a compressive device located within said sleeve, wherein said compressive device is engaged inside said sleeve between said proximal sleeve end and said proximal shaft end, wherein said compressive device is configured to gradually shorten along with said collapse of said shaft relative to said sleeve;
wherein said system is cannulated along its entire length; wherein said proximal sleeve end comprises a recessed region comprising a ledge; wherein said compressive device comprises a helical coil having one end abutting said ledge and a second end fixedly attached to said proximal shaft end; wherein said shaft and said sleeve rotate together by means of mating longitudinally extending flat surfaces on each of said sleeve and said shaft.

5. The system of claim 4, wherein said shaft comprises at least one of: a gripping device, a tip, cutting threads and fastening threads.

6. The system of claim 4, wherein said sleeve is configured with threads on an outside surface of said sleeve to facilitate rotating said sleeve into said first bone fragment.

7. The system of claim 4, wherein said sleeve includes additional openings for facilitating expansion of said sleeve.

8. The system of claim 4, wherein said shaft and said sleeve are substantially symmetrically aligned along a longitudinal axis.

9. The system of claim 4, wherein said proximal shaft portion has an end configured with a tool receiving component to receive a working end of a tool.

10. A method for maintaining a compressive load between a first bone fragment and a second bone fragment, said method comprising:
  inserting a distal portion of a shaft into a bore within said first bone fragment and said second bone fragment, through said first bone fragment and into said second bone fragment, wherein said shaft comprises a proximal shaft portion and distal head component, said proximal shaft portion is received into a sleeve prior to inserting into said bore, wherein said sleeve includes a proximal sleeve portion and a distal sleeve portion;
  increasing compression between said first bone fragment and said second bone fragment by continually advancing said distal head component into said second bone fragment such that said shaft translates distally from said proximal sleeve portion and a portion of said proximal shaft portion remains within said sleeve; and
  enabling said shaft to translate proximally within said sleeve in response to said first bone fragment and said second bone fragment being further compressed;
  wherein said proximal sleeve portion comprises a recessed region comprising a ledge; wherein a compression device comprises a helical coil having one end abutting said ledge and a second end fixedly attached to said proximal shaft portion; wherein said shaft and said sleeve rotate together by means of mating longitudinally extending flat surfaces on each of said sleeve and said shaft; wherein said sleeve and said shaft are cannulated along each of their lengths.

11. The method of claim 10, wherein said distal head component includes cutting threads and mating threads such that said inserting step includes cutting new threads into said second bone fragment using said cutting threads and mating said new threads with said mating threads.

12. The method of claim 10, further comprising forming at least three bores and inserting at least three of said shafts for rotational stability.

13. The system of claim 1, wherein said sleeve comprises a head portion which is configured to contact and be supported by a cortical portion of said first bone fragment.

14. The system of claim 1, wherein said shaft is retained within a cancellous bone portion of said second bone fragment.

15. The system of claim 1, wherein said sleeve further comprises an exterior surface, wherein at least a portion of said exterior surface is smooth and configured to rotate inside said first bone portion.

16. The system of claim 4, wherein said proximal shaft end is retained inside of said sleeve.

* * * * *